United States Patent
Rege et al.

(10) Patent No.: US 9,801,954 B2
(45) Date of Patent: Oct. 31, 2017

(54) LIPID SUBSTITUTION ON AMINOGLYCOSIDE BASED POLYMERS: PLASMID DELIVERY, ANTICANCER DRUG DELIVERY AND TRANSGENE EXPRESSION

(71) Applicants: Kaushal Rege, Chandler, AZ (US); Bhavani Miryala, Tempe, AZ (US); Thrimoorthy Potta, Phoenix, AZ (US)

(72) Inventors: Kaushal Rege, Chandler, AZ (US); Bhavani Miryala, Tempe, AZ (US); Thrimoorthy Potta, Phoenix, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/034,425

(22) PCT Filed: Nov. 5, 2014

(86) PCT No.: PCT/US2014/064017
§ 371 (c)(1),
(2) Date: May 4, 2016

(87) PCT Pub. No.: WO2015/069694
PCT Pub. Date: May 14, 2015

(65) Prior Publication Data
US 2016/0279264 A1    Sep. 29, 2016

Related U.S. Application Data

(60) Provisional application No. 61/899,986, filed on Nov. 5, 2013.

(51) Int. Cl.
*A61K 48/00* (2006.01)
*A61K 47/48* (2006.01)
*C12N 15/87* (2006.01)

(52) U.S. Cl.
CPC ...... *A61K 48/0041* (2013.01); *A61K 47/4823* (2013.01); *A61K 47/48046* (2013.01); *A61K 47/48192* (2013.01); *C12N 15/87* (2013.01)

(58) Field of Classification Search
CPC .......... A61K 48/0041; A61K 47/48192; A61K 47/48046; A61K 47/4823; C12N 15/87
See application file for complete search history.

(56) References Cited

U.S. PATENT DOCUMENTS 5,151,264 A     9/1992  Samain et al.
2012/0196923 A1  8/2012  Rege et al.

FOREIGN PATENT DOCUMENTS

WO        2013055971     4/2013
WO     WO2013055971     4/2013

OTHER PUBLICATIONS

Zhang, N. et al. Polysaccharide-Based Micelles for Drug Delivery. Pharmaceutics. 2013, 5, 329-352.
Liu, Z et al. Hydrophobic modifications of cationic polymers for gene delivery. Progress in Polymer Science. 2010, 35, 1144-1162.
Termsarasab, U et al. Chitosan oligosaccharide-arachidic acid-based nanoparticles for anti-cancer drug delivery. International Journal of Pharmaceutics. 2013, 441, 373-380.
Layek, B et al. Caproic acid grafted chitosan cationic nanocomplexes for enhanced gene delivery: Effect of degree of substitution. International Journal of Pharmaceutics. 2013, 447, 182-191.
Yu, J et al. Fabrication and characterization of nuclear localization signal-conjugated glycol chitosan micelles for improving the nuclear delivery of doxorubicin. International Journal of Nanomedicine. 2012, 7, 5079-5090.
Hu, F et al. Effective antitumor gene therapy delivered by polyethylenimine conjugated stearic acid-g-chitosan oligosaccharide micelles. Gene Therapy. 2013, 20, 597-606.
Potta, T et al Discovery of Antibiotics-derived Polymers for Gene Delivery using Combinatorial Synthesis and Cheminformatics Modeling. Biomaterials. 2014, 35, 1977-1988.
Blaese, R. M. et al. T lymphocyte-directed gene therapy for ADA-SCID: Initial trial results after 4 years. Science. 1995, 270, 475-480.
Boztug, K et al. Stem-cell gene therapy for the wiskott-aldrich syndrome. N. Engl. J. Med. 2010, 363,1918-1927.
Cavazzana-Calvo, M et al. Gene therapy of human severe combined immunodeficiency (SCID)-X1 disease. Science. 2000, 288, 669-672.
Aiuti, A et al. Gene therapy for immunodeficiency due to adenosine deaminase deficiency. N. Engl. J. Med. 2009, 360, 447-458.
Boussif, O et al. A versatile vector for gene and oligonucleotide transfer into cells in culture and in vivo: Polyethylenimine. Proc. Natl. Acad. Sci. U. S. A. 1995, 92, 7297-7301.
Kircheis, R et al. Design and delivery activity of modified polyethylenimines. Adv. Drug Deliv. Rev. 2001, 53, 341-358.
El-Aneed, A. Current strategies in cancer gene therapy. J. Control. Release, 2004, 498,1-8.
Wang, Y.X. et al. Progress in non-viral gene delivery systems fabricated via supramolecular assembly. Chin. Sci. Bull. 2005, 50, 289-294.
Liu, W.G. et al. An investigation on the physicochemical properties of chitosan/DNA polyelectrolyte complexes. Biomaterials. 2005, 26, 2705-2711.
Lorenz, C. et al. Steroid and lipid conjugates of siRNAs to enhance cellular uptake and gene silencing in liver cells. Bioorg Med Chem Lett. 2004, 14, 4975-4977.
Wolfrum, C et al. Mechanisms and optimization of in vivo delivery of lipophilic siRNAs. Nat Biotechnol. 2007, 25, 1149-1157.
Soutschek, J et al. Therapeutic silencing of an endogenous gene by systemic administration of modified siRNAs. Nature. 2004, 432,173-178.
Morrissey, D.V. et al. Potent and persistent in vivo anti-HBV activity of chemically modified siRNAs. Nat Biotechnol. 2005, 23, 1002-1007.

(Continued)

*Primary Examiner* — Robert Jones, Jr.
(74) *Attorney, Agent, or Firm* — Gavin J. Milczarek-Desai; Quarles & Brady LLP

(57) ABSTRACT

A method to form a lipid-containing aminoglycoside-based polymer, where the method includes reacting an aminoglycoside with a diepoxide to form an aminoglycoside-based polymeric material, and then reacting the aminoglycoside-based polymeric material with an acyl chloride to form the lipid-containing aminoglycoside-based polymer.

16 Claims, 25 Drawing Sheets

(56) References Cited

OTHER PUBLICATIONS

Nishina, K et al. Efficient in vivo delivery of siRNA to the liver by conjugation of α-tocopherol. Mol Ther. 2008, 16,734-740.

Tseng, Y.C. et al. Lipid-based systemic delivery of siRNA. Adv Drug Deliver Rev. 2009, 61,721-731.

Luyanov, A.N. et al. Micelles from lipid derivatives of water-soluble polymers as delivery systems for poorly soluble drugs. Advanced Drug Delivery Reviews. 2004, 56, 1273-1289.

Munk, P et al. Exploiting polymer micelle technology. CHEMTECH. 1998, 28, 20-28.

La, S.B. et al. Preparation and characterization of the micelle-forming polymeric drug indomethacin-incorporated poly (ethylene oxide)-poly(β-benzyl l-asparate) block copolymer micelles. J. Pharm. Sci. 1996, 85, 85-90.

Kabanov, A.V. et al. Pluronic block copolymers as novel polymer therapeutics for drug and gene delivery. J. Control. Release. 2002, 82, 189-212.

Woflert, M.A. et al. Characterization of vectors for gene therapy formed by self-assembly of DNA with synthetic block co-polymers. Hum. Gene Ther.1996, 7, 2123-2133.

Katayose, S et al. Water-soluble polyion complex associates of DNA and poly (ethylene glycol)-poly(L-lysine) block copolymer. Bioconjug. Chem. 1997, 8, 702-707.

Katayose, S et al. Remarkable increase in nuclease resistance of plasmid DNA through supramolecular assembly with poly (ethylene glycol)-Poly(L-lysine) block copolymer. J. Pharm. Sci. 1998, 87, 160-163.

International search report and written opinion of international application No. PCT/US 14/64017 filed on Nov. 5, 2014.

FIG. 1A

| ID | Structure | Name |
|---|---|---|
| A | 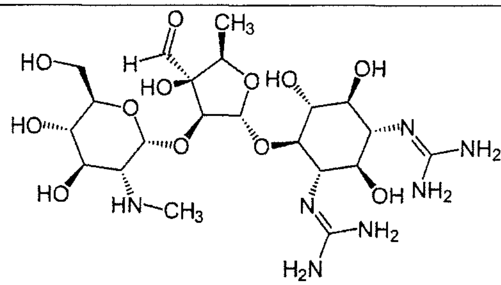 | Streptomycin |
| B | 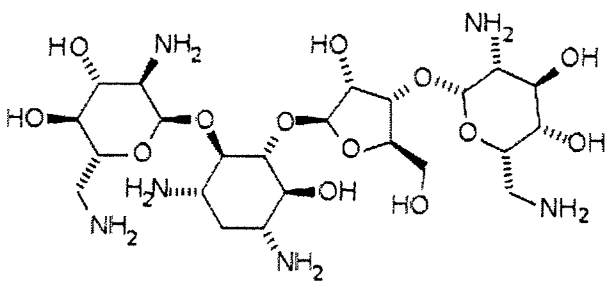 | Neomycin |
| C | 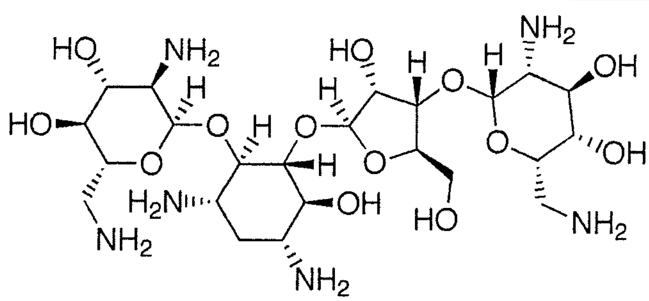 | Framycetin |
| D | 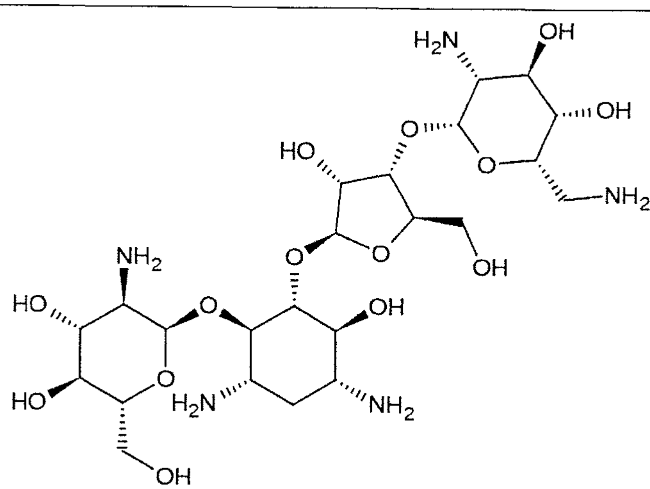 | Paromomycin |

FIG. 1B

| | | |
|---|---|---|
| E | (structure) | Ribostamycin |
| F | (structure) | Kanamycin |
| G | (structure) | Amikacin |
| H | (structure) | Arbekacin |

FIG. 1C

| | | |
|---|---|---|
| I | *(structure)* | Bekanamycin |
| J | *(structure)* | Dibekacin |
| K | *(structure)* | Tobramycin |
| L | *(structure)* | Spectinomycin |
| M | *(structure)* | Hygromycin b |

FIG. 1D

| | | |
|---|---|---|
| N | (structure) | Gentamicin |
| O | (structure) | Netilmicin |
| P | (structure) | Sisomicin |
| Q | (structure) | Isepamicin |
| R | (structure) | Verdamicin |

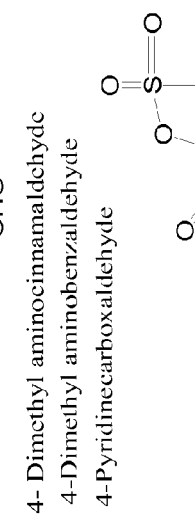
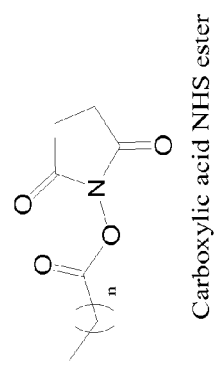
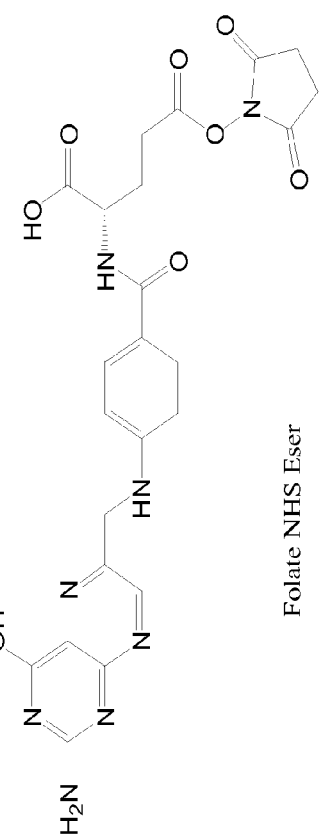
FIG. 3B

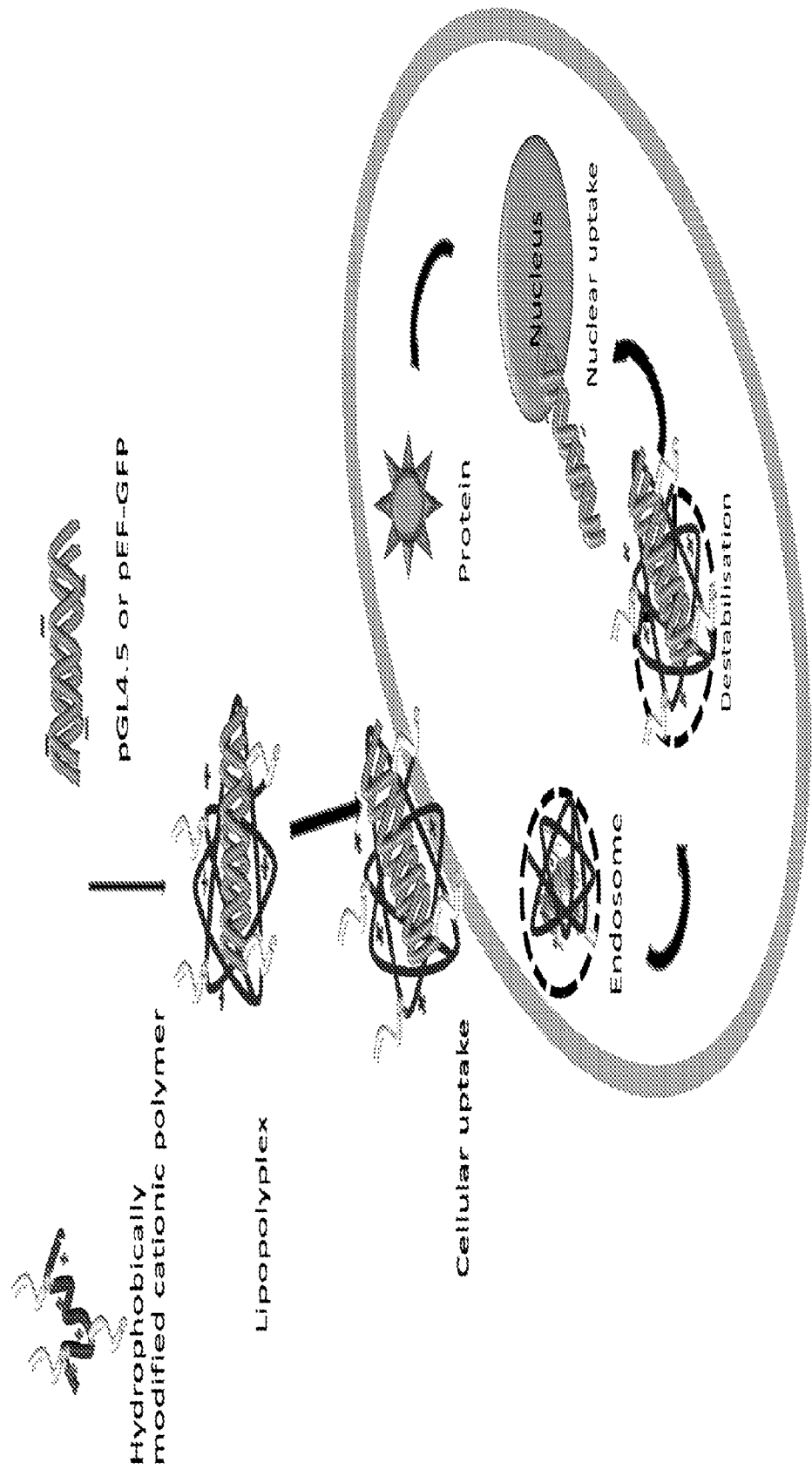

LIPID SUBSTITUTION ON AMINOGLYCOSIDE BASED POLYMERS: PLASMID DELIVERY, ANTICANCER DRUG DELIVERY AND TRANSGENE EXPRESSION

CROSS-REFERENCE TO RELATED APPLICATIONS

This application is a 371 application of PCT/US2014/064017 filed Nov. 5, 2014, which is based on, claims a priority benefit from, and incorporates herein by reference, U.S. Provisional Patent Application No. 61/899,986, filed Nov. 5, 2013, and entitled "Lipid Substitution on Aminoglycoside Based Polymers: Plasmid Delivery, Anticancer Drug Delivery and Transgene Expression."

STATEMENT REGARDING FEDERALLY SPONSORED RESEARCH

This invention was made with government support under R01 GM093229 awarded by the National Institutes of Health. The government has certain rights in the invention.

FIELD OF THE INVENTION

A library of lipid modified polymers formed by conjugation of lipid acid chlorides with a polymer, a method of preparing the same, and a use thereof are provided.

BACKGROUND OF THE INVENTION

Gene therapy is a powerful approach for the treatment of hereditary and acquired diseases. The two main types of delivery systems for gene delivery are the viral and the non-viral systems. Due to the safety concerns associated with viral vectors non-viral systems had attained increasing importance over period of time.

Cationic liposomes and cationic polymers are two main types of non-viral vectors. Low cost, flexibility in chemical design and safety are some of the advantages of non-viral vectors over viral based vectors. Nevertheless, they also have some disadvantages like low gene expression and toxicity.

BRIEF DESCRIPTION OF THE DRAWINGS

The invention will be better understood from a reading of the following detailed description taken in conjunction with the drawings in which like reference designators are used to designate like elements, and in which:

FIGS. 1A-1E recite a listing of aminoglycosides used to synthesize polymers;

FIGS. 3A-B recite a listing of lipids used to conjugate to the polymers;

FIG. 4 graphically illustrates steps involved in lipid modified polymer gene delivery;

DETAILED DESCRIPTION OF THE INVENTION

Figure 1E:
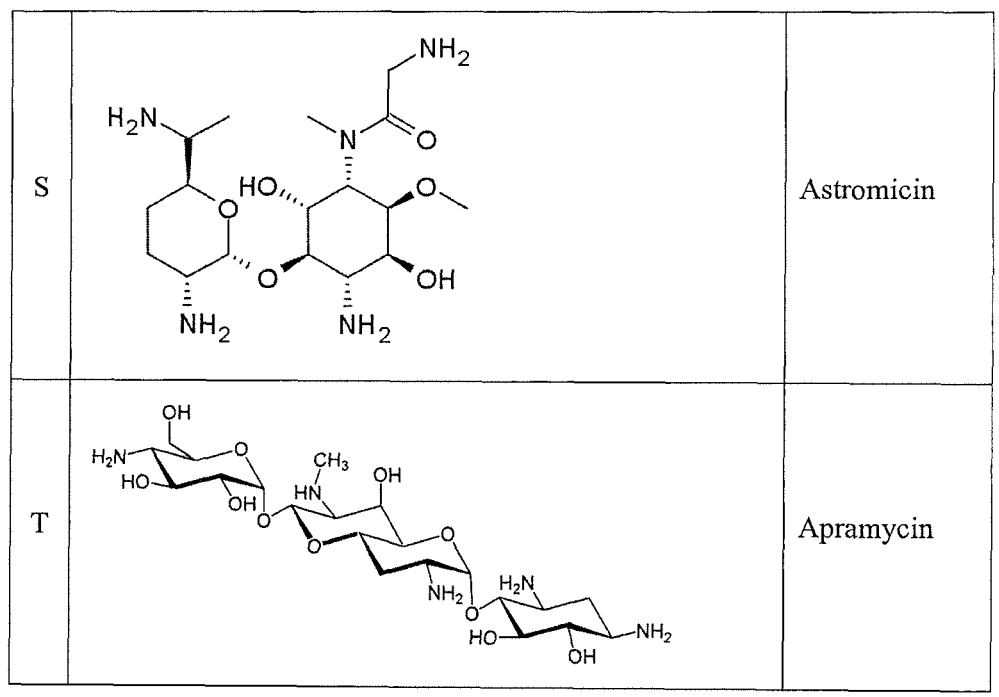
Figure 2:
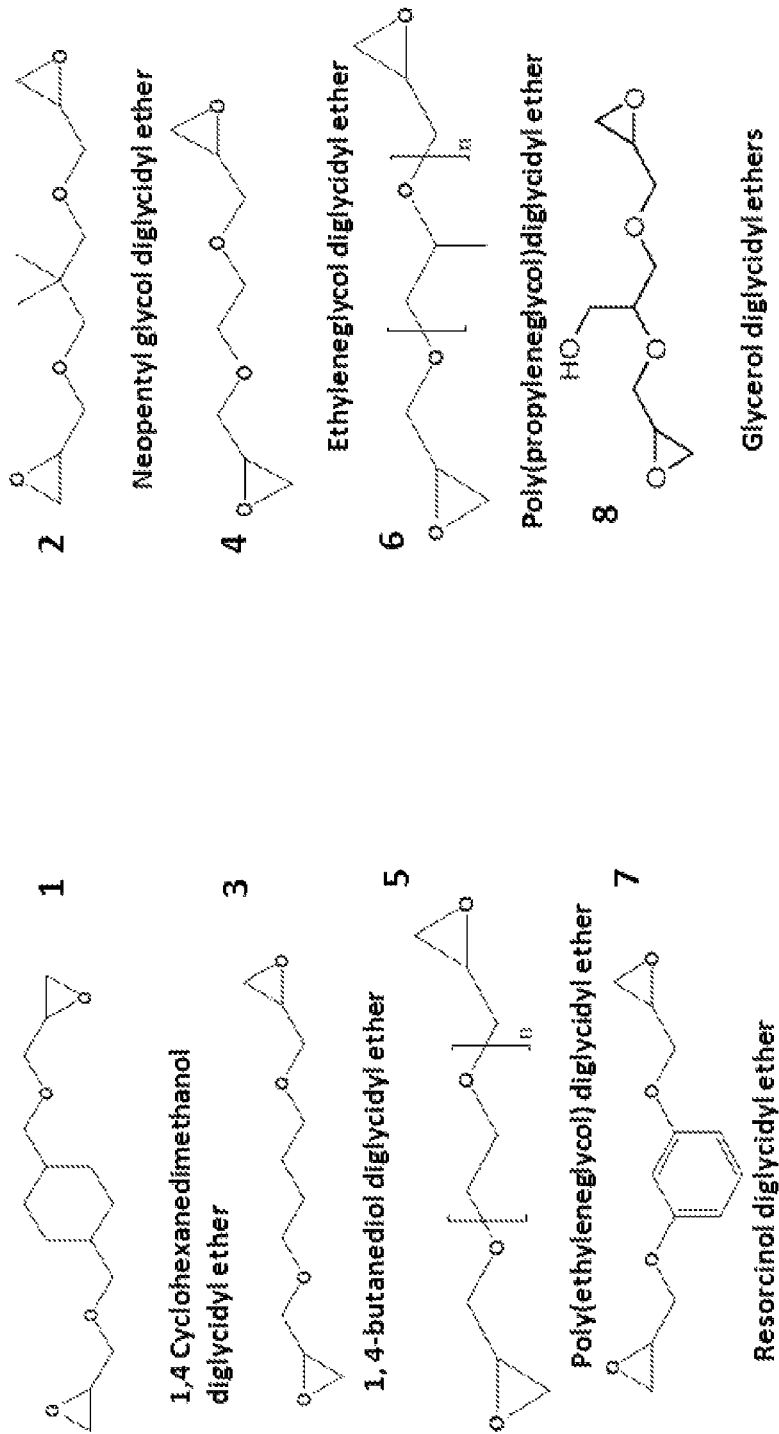
FIG. 2 recites a listing of cross-linkers used to synthesize polymers.
Figure 3A:
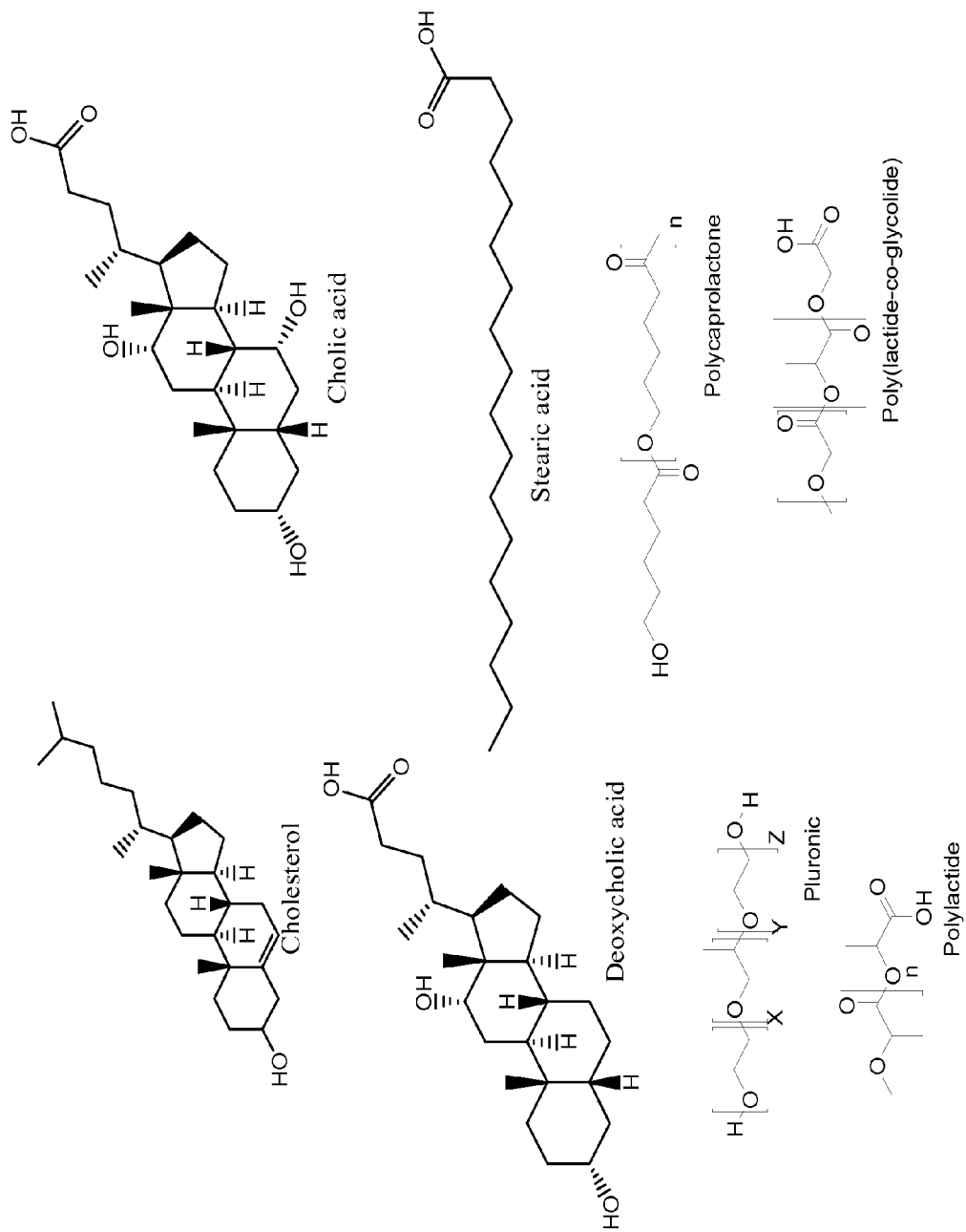
Figure 5A:
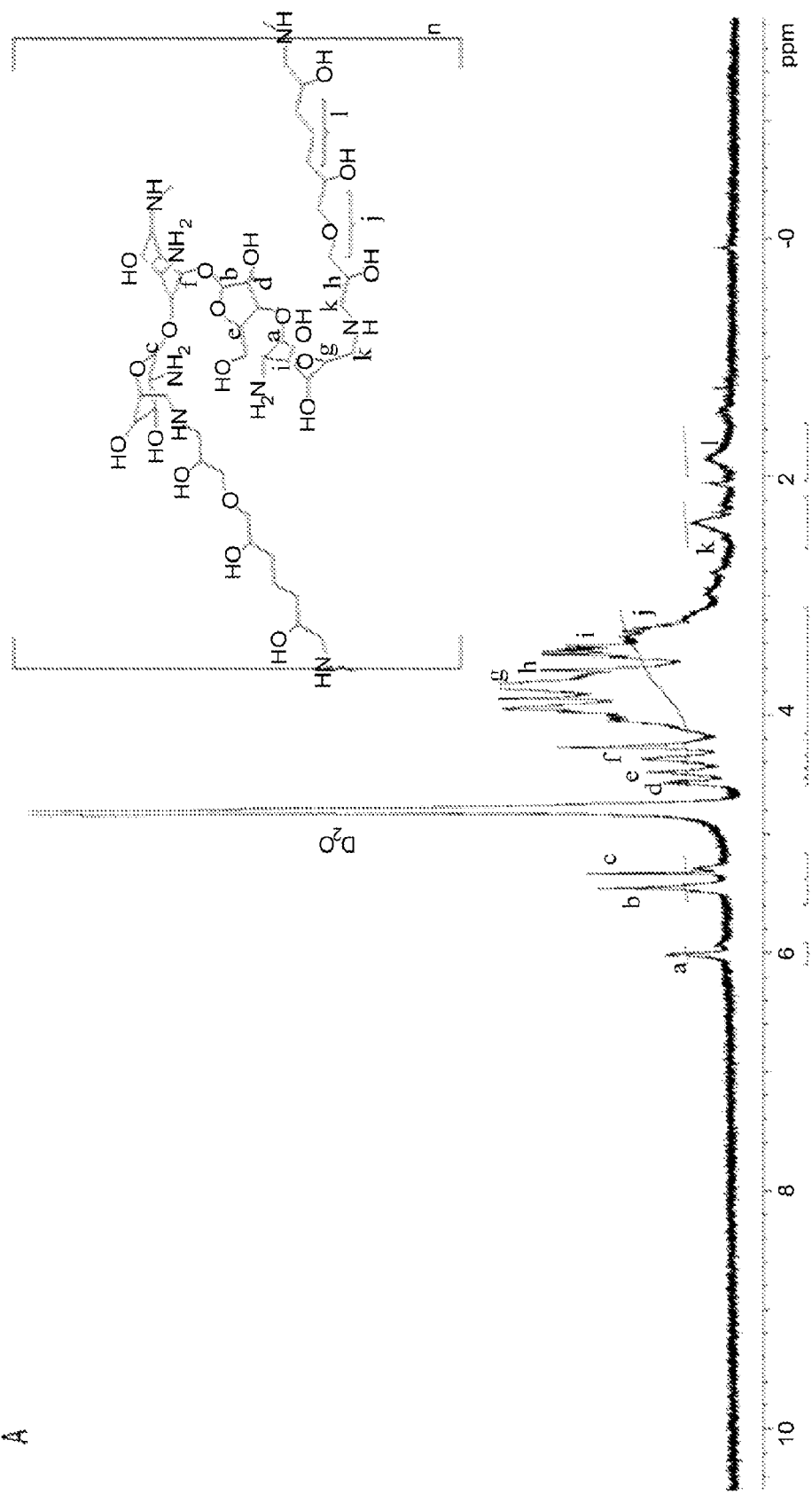
FIG. 5A recites a proton NMR spectrum of a Neomycin-GDE polymer.
Figure 5B:
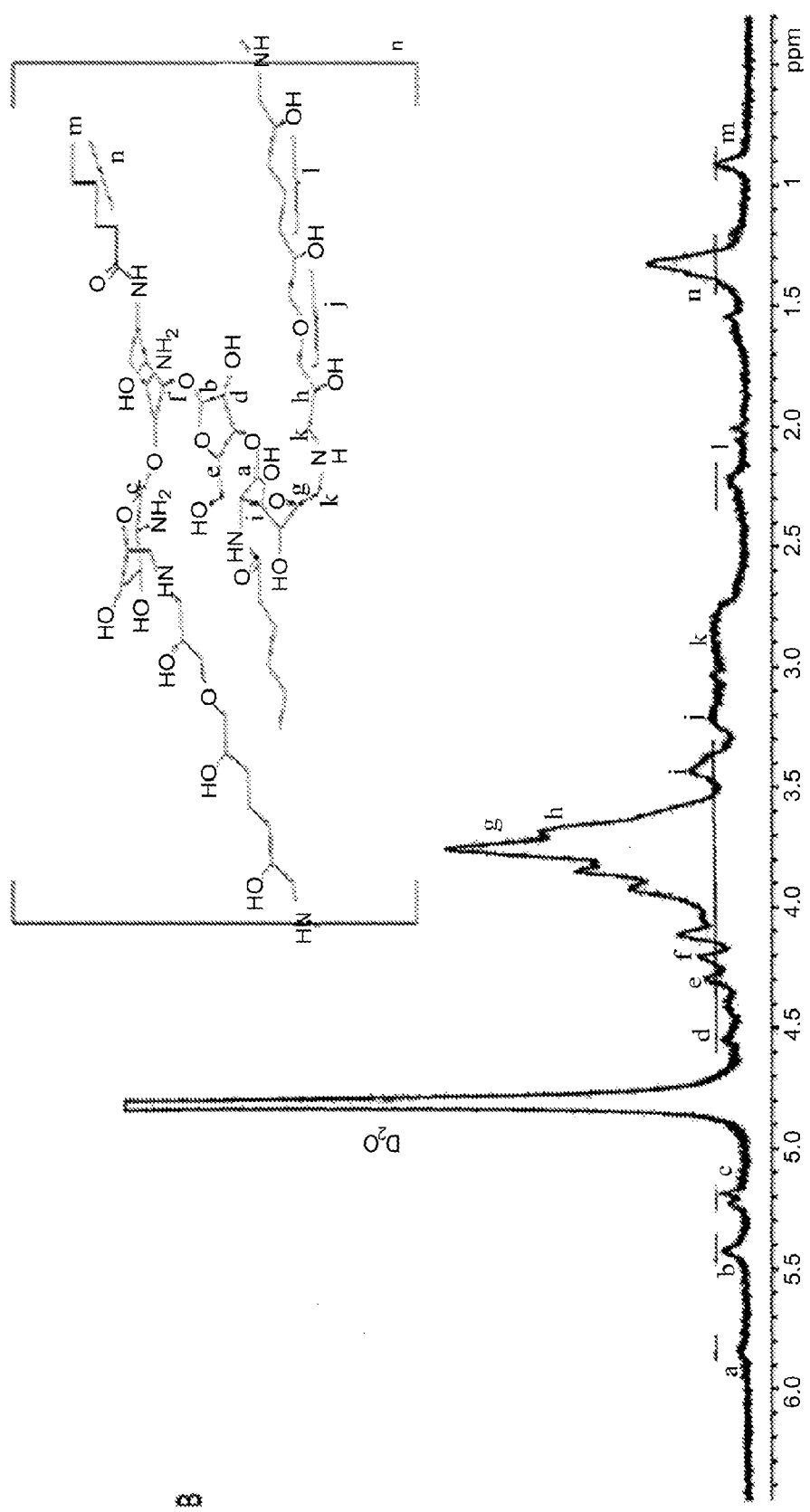
FIG. 5B recites a proton NMR spectrum of a Neomycin-GDE polymer conjugated with hexanoyl chloride.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

To overcome the limitations associated with cationic polymers, several combinations of cationic amines and cationic lipids have been tried. Among them the amphiphilic polymers formed by the conjugation of lipidic moieties on to the polymer are more attractive, since they have the beneficial effects of nucleic acid condensation from cationic polymers and compatibility with cellular membranes from lipid moieties in single carrier system. Cationic polymers substituted with various hydrophobic molecules are found to show improved gene delivery activity when compared to parent polymers. Introduction of hydrophobic chain can not only effect the interaction with the plasma membrane but also can affect at most steps during the whole gene delivery process.

Applicants identified antibiotics-derived polymers for gene delivery using combinatorial synthesis and cheminformatics modeling. The library of polymers prepared by parallel synthesis was evaluated for in-vitro gene transfection studies in multiple kinds of cancer cells using plasmid DNA. The transfection efficacies of few of the leads were found to be many times higher than poly (ethyleneimine) used as standard. With an insight into further improvisation of transfection profiles of the developed polymers, few of the leads were selected and used for hydrophobic modifications.

Applicants developed a library of lipid modified aminoglycoside based polymers by simple N-acylation reaction. As those skilled in the art will appreciate, an "aminoglycoside" comprises an amino-modified sugar.

Hexanoyl chloride, Myristyl chloride and Stearyl chloride were choosen as the hydrophobic segments to synthesize the amphiphilic grafted polymers. The gene delivery efficacies of the developed conjugates were tested in different types of cancer cells. The objective of this study was to elucidate changes in properties of polymer-DNA complexes as a result of lipid substitution and to access the effect of lipid substitution on the effectiveness in transgene expression.

1. Synthesis and Characterization of Lipid-substituted Polymers.

(a) Synthesis of Polymers:

A library of 54 lipid conjugates of polymers was synthesized with three different lipid acid chlorides in three different molar ratios. The polymers synthesized were dissolved in DMSO(Dimethyl sulfoxide) (2 mL) at room temperature by stirring for 30 min and triethyl amine (in 1:4 molar ratio with respect to polymer) was added to the solution and stirred for an additional 30 min period. The mixture was then cooled to 4° C. and different amounts of alkanoyl cholorides (1:2, 1:5, 1:10 corresponding to different molar ratios with respect to polymer) were added drop wise and the mixture was stirred at room temperature for 12 h. The final product was collected by precipitation in excess ether. The product was further purified by dialysis using a 3500 molecular weight cutoff (MWCO) membrane to remove unreacted polymer, any traces of triethylamine and DMSO. The dialyzed material was lyophilized to obtain the lipopolymer product. Synthetic procedure showing lipid modification of polymers is shown in Scheme 1.

Scheme 1 summarizes the synthetic procedure for preparing Applicants' polymeric materials.

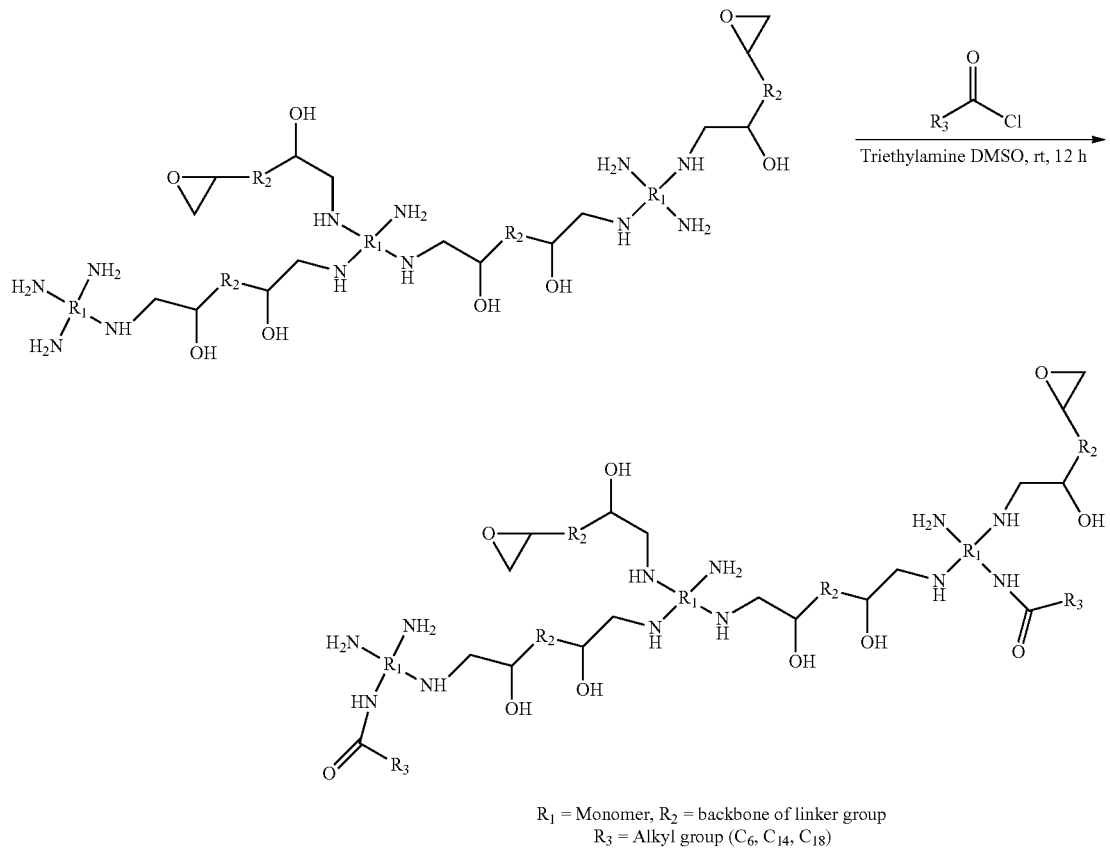

$R_1$ = Monomer, $R_2$ = backbone of linker group
$R_3$ = Alkyl group ($C_6$, $C_{14}$, $C_{18}$)

The structural composition of the lipid-substituted polymers was analyzed by

1H NMR (Bruker 300 MHz, Billerica, Mass.) in $D_2O$ and DMSO. 1H NMR analysis showed the expected alkanoyl protons —CH3 (δ 0.8 ppm), -γ-CH2 (δ 1.26-ppm), -β-CH2 (δ 1.6 ppm), -α-CH2 (δ2.16 ppm), in the obtained polymers. The characteristic resonance shifts corresponding to alkyl chain-CH3 (δ 0.8 ppm), and Polymer (CH— δ 5.6 ppm) were used to obtain the extent of lipid substitution. The number of grafted lipids generally increased with increasing feed ratio. Table 1 shows the feed molar ratios, the ratios calculated from NMR and the degree of lipid substitution of the lead lipid conjugated polymers.

Gel permeation chromatography (GPC) was employed for determining lipid conjugated polymers molecular weights. A Waters 1515 GPC system, in concert with an ultrahydrogel 250 column (Waters Corporation, MA) and a refractive index detector (Waters 2410), was used. An aqueous solvent containing 0.1% trifloroacetic acid and 40% acetonitrile was used as the mobile phase. The molecular weights of lead lipid conjugated polymers (picked up from in vitro transgene expression screening in PC3 cells) was determined using GPC and is found that the average molecular weights are in the range of 4.0-6.0 kDa. Molecular weights of leads are shown in Table 2. Lead lipid polymer conjugates exhibited varying amine concentrations, which are dependent on the number of amines in the parental polymers. The polydispersities of the lead lipid conjugated polymers range from 1.1-1.3 which shows the lipid conjugated polymers are relatively homogeneous and are found to be more homogeneous when compared to the parent polymers.

Hydrodynamic sizes and zeta potentials of lipid conjugated polymers and lipid conjugated polymer-pDNA complexes (lipopolyplexes) were determined using a Zetasizer Nanosystems Nano-ZS instrument (Malvern Instruments, Mission Viejo, Calif.). Lead lipopolymer-pDNA complexes were prepared at DNA: lipopolymer weight ratios of 1:5 to 1:50 by adding different amounts of polymers to 100 ng of DNA. Zeta potential and size distribution measurements were carried out in triplicate after mixing the polymer and pDNA solutions for 20 minutes at room temperature.

Polymer charge plays an important role in polyplex formation; positive charges on the polymer interact with negative charges in pDNA, by means of electrostatic interactions, ultimately resulting in the formation of nanoscale polymer-pDNA complexes or polyplexes. Positively charged polyplexes are efficiently taken up by cells, ultimately resulting in transgene expression. In the present invention we found that the lipid conjugated polymers which have glycerol diglycidyl ether as linker group in their polymer synthesis (Paromomycin-GDE, Neomycin-GDE and Apramycin-GDE) are polydisperse whereas the lipid conjugated polymers which have resorcinol diglycidyl ether as linker group in their polymer synthesis (Paromomycin-RDE, Neomycin-RDE and Apramycin-RDE) are nanoparticles and exhibited micellar properties.

Hydrophobically grafted polymers assemble into a core-shell micelle structure, creating the potential to load hydrophobic drugs and gene drugs into the different compartments (core and shell) respectively. Some examples include poly (e-caprolactone)-bPEI 1.8 kDa, poly((Nmethyldietheneamine sebacate)-co-[(cholesteryl oxocarbonylamidoethyl) methyl bis(ethylene)ammonium bromide]sebacate), and poly(dimethylaminoethyl methacrylate)-poly(e-caprolactone)-poly(dimethylaminoethyl methacrylate). Other advantages of polymeric micelles include their low critical micelle concentrate (CMC) value which promotes greater stability in aqueous environments. 18,19 Thus the emerging polymeric micellar DNA carriers include hydrophobically modified water-soluble polymers.

Figure 6A:
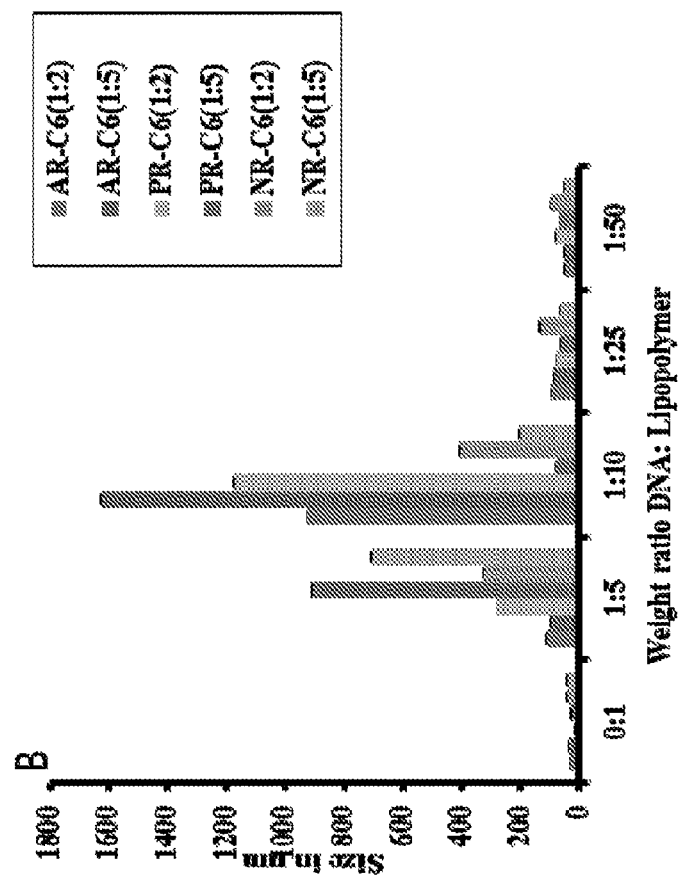
FIG. 6A graphically shows hydrodynamic sizes for lipopolymers with Glycerol diglycidyl ether as linker group.
Figure 6B:
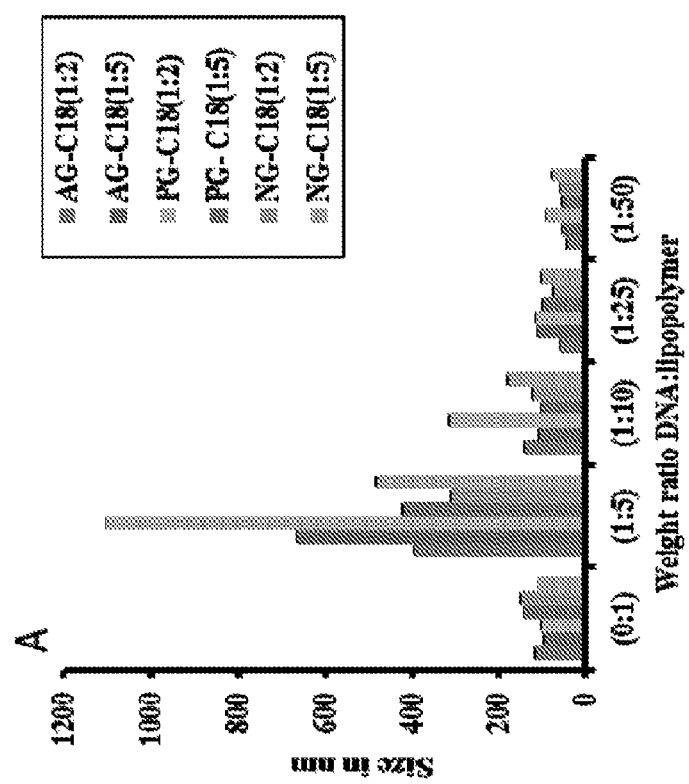
FIG. 6B graphically shows hydrodynamic sizes for lipopolymers with Resorcinol diglycidyl ether as linker group.
Figure 7B:
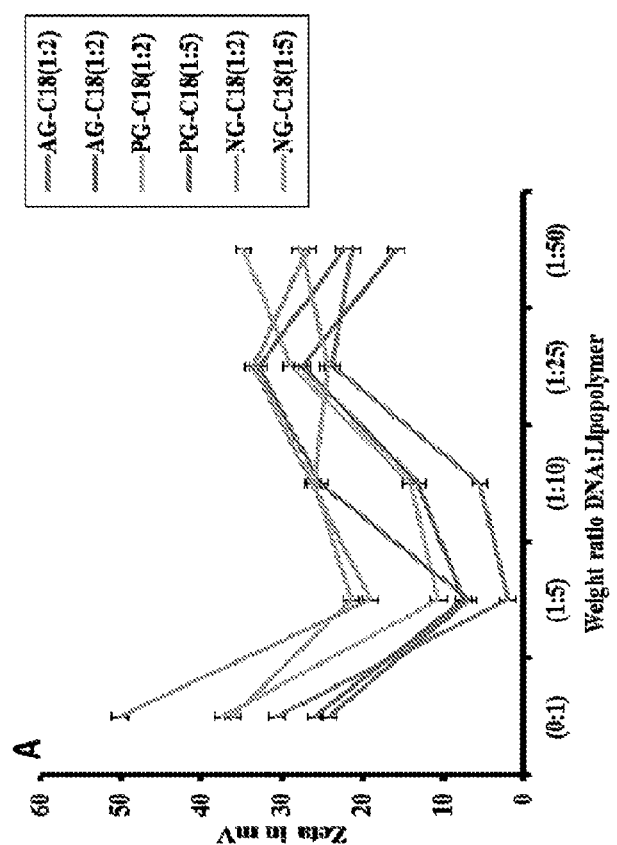
FIG. 7B graphically shows Zeta potential values of leads of lipopolymers with Resorconol diglycidyl ether as a linker group.
Figure 7A:
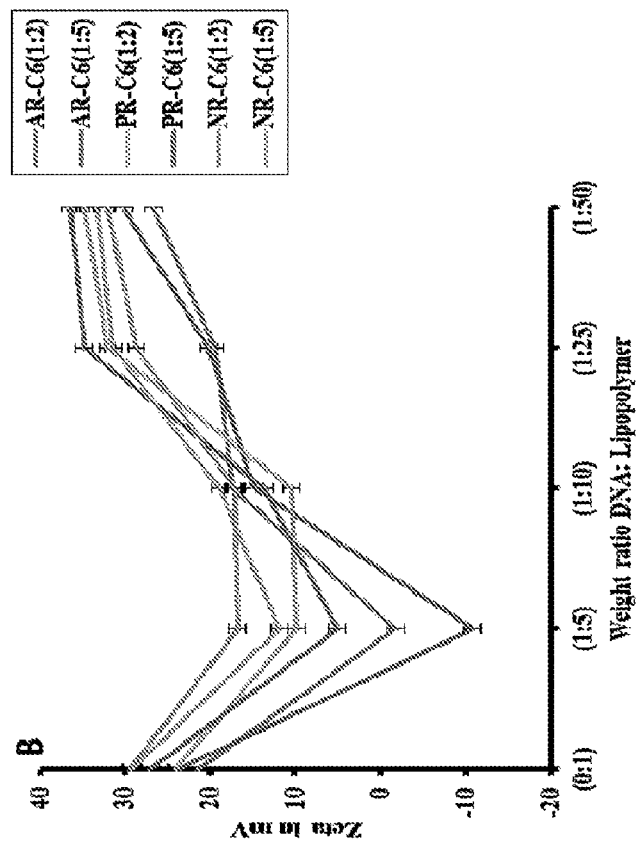
FIG. 7A graphically shows Zeta potential values of leads of lipopolymers with Glycerol diglycidyl ether as a linker group.
Figure 8:
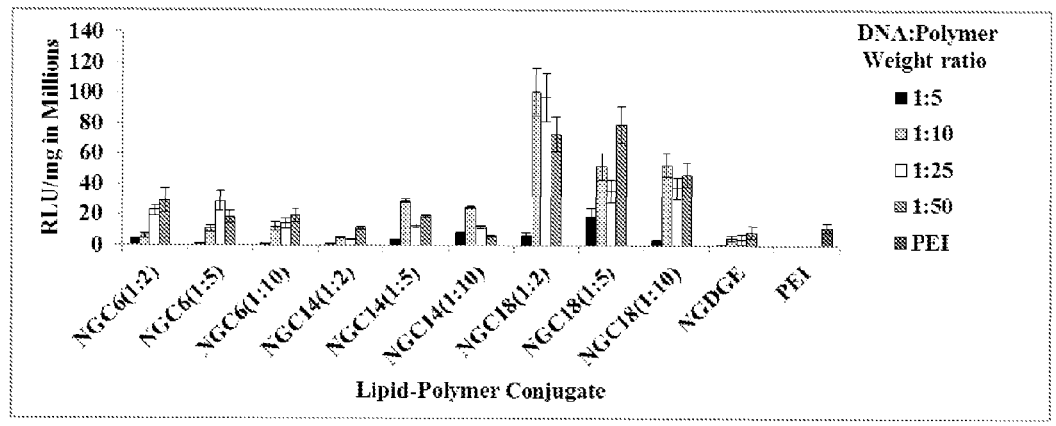
FIG. 8 graphically illustrates in vitro transfection profiles of Neomycin-GDE polymer, Neomycin-GDE lipid polymer conjugates with varying lipids and varying molar ratios and pEI at different weight ratios in PC3 cells.
Figure 9:
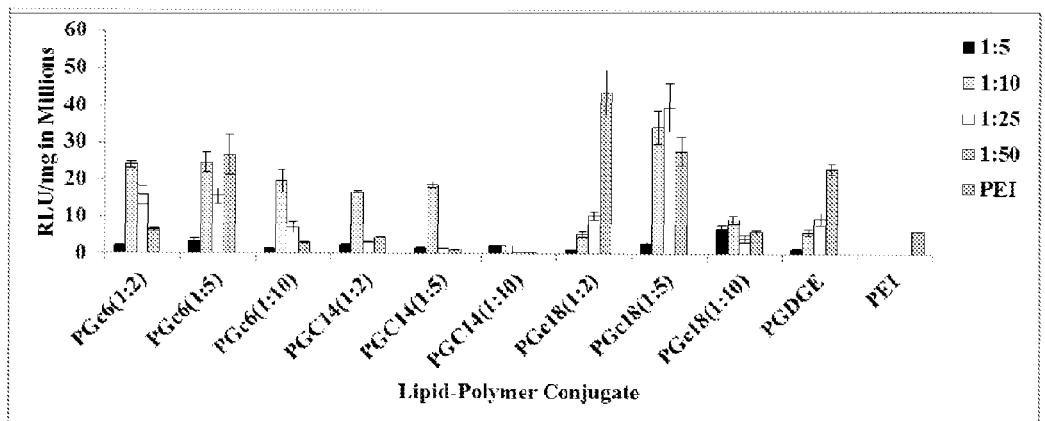
FIG. 9 graphically illustratrates in vitro transfection profiles of Paromomycin-GDE polymer, Paromomycin-GDE lipid polymer conjugates with varying lipids and varying molar ratios and pEI at different weight ratios in PC3 cells.
Figure 10:
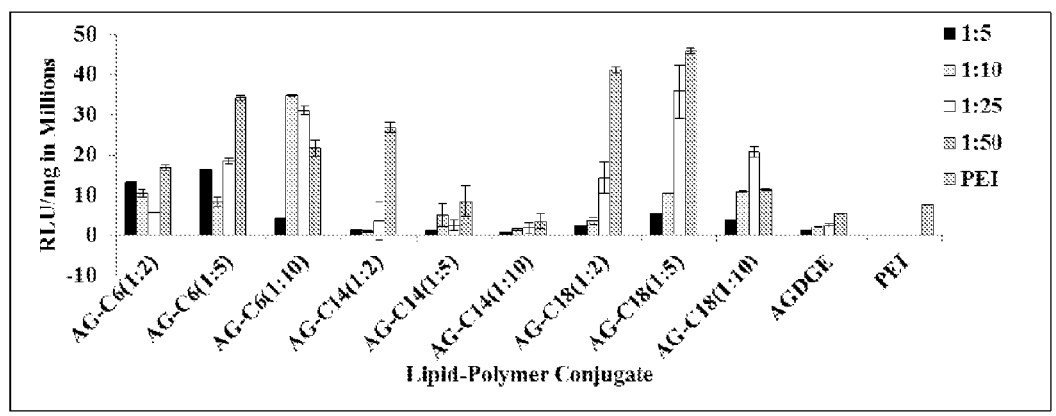
FIG. 10 graphically illustratrates in vitro transfection profiles of Apramycin-GDE polymer, Apramycin-GDE lipid polymer conjugates with varying lipids and varying molar ratios and pEI at different weight ratios in PC3 cells.
Figure 11:
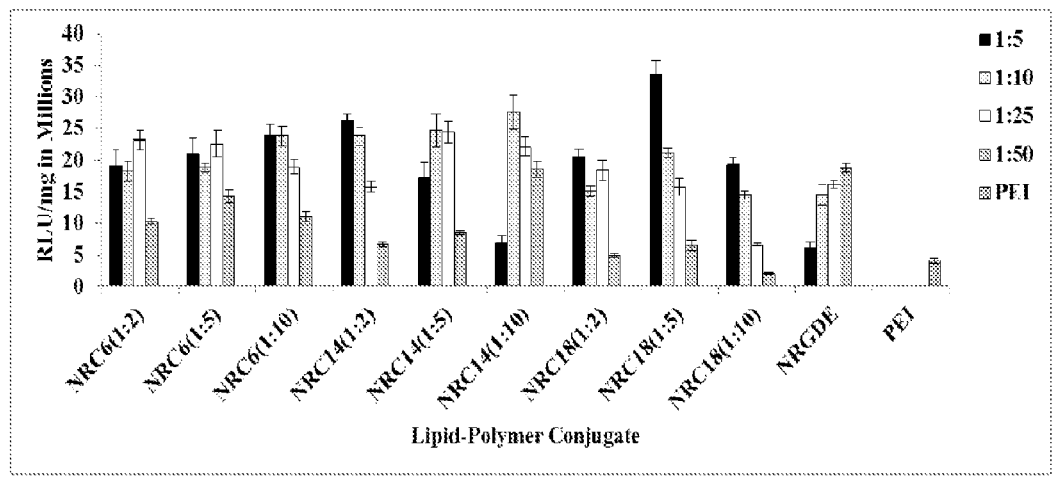
FIG. 11 graphically illustratrates in vitro transfection profiles of Neomycin-RDE polymer, Neomycin-RDE lipid polymer conjugates with varying lipids and varying molar ratios and pEI at different weight ratios in PC3 cells.
Figure 12:
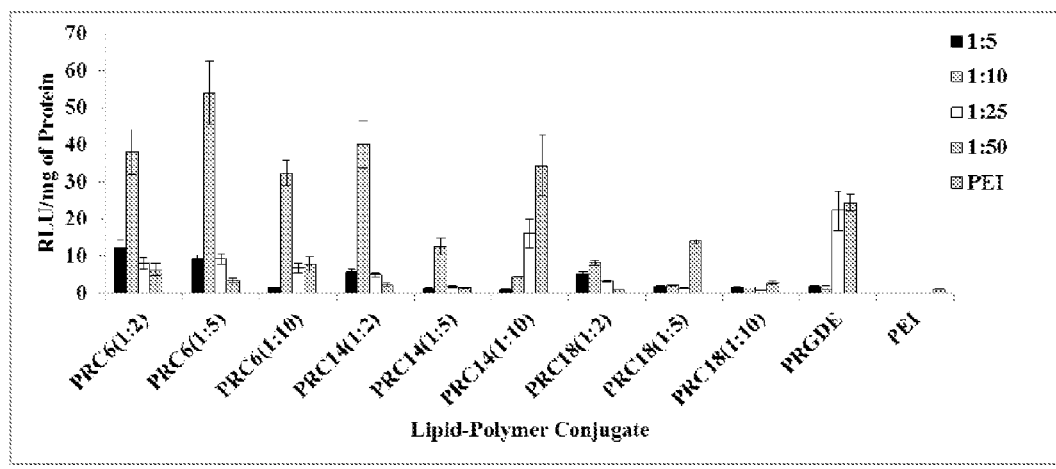
FIG. 12 graphically illustratrates in vitro transfection profiles of Paromomycin-RDE polymer, Paromomycin-RDE lipid polymer conjugates with varying lipids and varying molar ratios and pEI at different weight ratios in PC3 cells.
Figure 13:
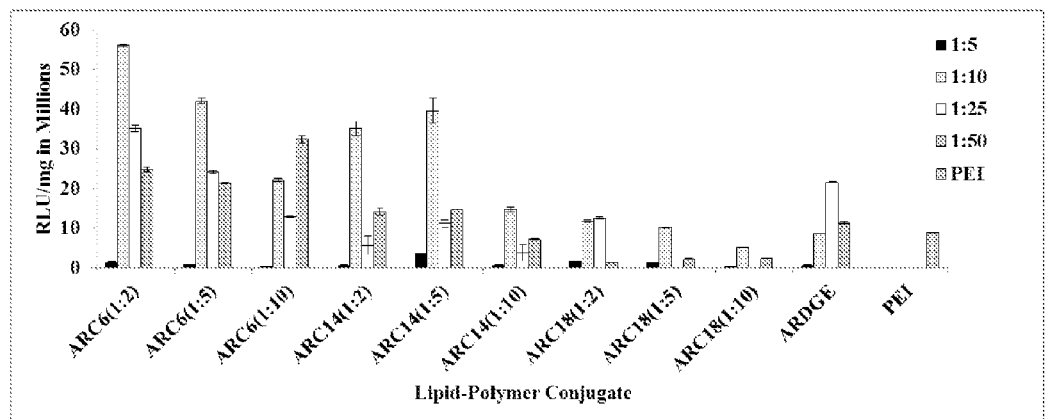
FIG. 13 graphically illustratrates in vitro transfection profiles of Apramycin-RDE polymer, Apramycin-RDE lipid polymer conjugates with varying lipids and varying molar ratios and pEI at different weight ratios in PC3 cells.

The micellar systems developed can have the advantages not only in the field of gene delivery (as studied in the present invention) but also have various other biomedical applications like drug delivery, imaging studies etc. 20-12 The sizes and zeta potentials of the leads from two different sets of lipid conjugated polymers based on their particle nature are shown in FIGS. 6,7.

In the present invention we found that the hydrodynamic size and zeta potential of pDNA/polymer complexes (using plasmid pGL4.5) showed significant changes as a result of lipid substitution on the polymers. The pDNA/Polymer mass ratio used to form complexes was a significant factor of the hydrodynamic size, more so than the extent of lipid substitution on the polymers. At lower pDNA/polymer ratios (1:5, 1:10) the hydrodynamic sizes of the lipid-substituted complexes were generally larger than the complexes formed with the corresponding native lipid-substituted polymers. At higher pDNA: polymer ratios (1:25, 1:50) the size of all complexes (<100 nm) was uniformly smaller than the native lipid-conjugated polymers.

The increase in the hydrodynamic size likely reflects the consequences of lower polyamine content necessary for pDNA condensation. The decrease in complex size was presumably driven by the high lipid content in the complexes, facilitating stronger hydrophobic associations among the lipids and resulting in more compact particles.

The influence of lipid substitution was clearly evident on the zeta potential of complexes. The zeta potential of the native lipid-substituted polymers are found to be higher compared to the pDNA/polymer complexes. The mass ratio of pDNA/Polymer also influenced the zeta potential of complexes (increasing zeta potential with increasing mass ratio).

The aminoglycoside-based lipopolymer library was screened in parallel for delivering the pGL4.5 control vector (Promega Corp., Madison, Wis.), which encodes for the modified firefly luciferase protein, to different cancer cell lines. The pGL4.5 plasmid DNA (pDNA) was prepared as described previously. Plasmid concentration and purity were determined using a NanoDrop Spectrophotometer (ND-1000; NanoDrop Technologies) by measuring absorbance at 260 and 280 nm.

Prostate cancer cells (PC3, PC3-PSMA and 22RV1) and bladder cancer cells (MB49) were used for the in vitro transfection experiments. Cells were seeded at a density of 9000 per well in a 96-well plate 18-24 hours before the transfection using RPMI-1640 media. 100 ng of plasmid DNA was complexed with varying amounts of lipopolymers in HEPES buffer for 30 minutes. The weight ratios were varied from 1:5 to 1:50 over these ranges of the polymers. Just prior to transfection, cells plated in the 96-well plate were washed with PBS (2×100 μL) followed by the addition of polyplexes. After 6 h of incubation, 150 μL of Serum containing media was added to the cells.

After 48 h of further incubation in serum-containing media, cells were lysed, and luciferase protein expression was determined as relative luminescence units (RLU) using the Bright GloTM Luciferase assay kit (Promega) with a plate reader (Bio-Tek Synergy 2). Cell lysates were then assayed for total protein content using the BCA Protein Assay kit (Pierce, Rockford, Ill., USA). RLU values were normalized by the protein content to yield 'RLU/mg protein' values that were employed for comparing different polymers. Untransfected cells and cells transfected with uncomplexed pDNA were used as controls. Luciferase expression efficacies of polymers from the library were compared to that with 25 kDa branched pEI. In all cases, the pEI solution was prepared fresh right before all transfection experiments.

Preliminary screening of luciferase transgene expression of all the 54 conjugates at varying pDNA/lipopolymer was done with PC3 type of cell line. The transgene expression of all the lipid conjugated polymers were evaluated with respect to the parent polymer and the pEI-25 kDa. Twelve leads were picked up from the initial screening and were further evaluated for transgene expression in other types of cell lines. The data of in vitro transgene expression in PC3 cells is given in FIGS. 8-13. The data is plotted separately for the two different sets of lipopolymers and their leads based on their particle nature.

Figure 14:
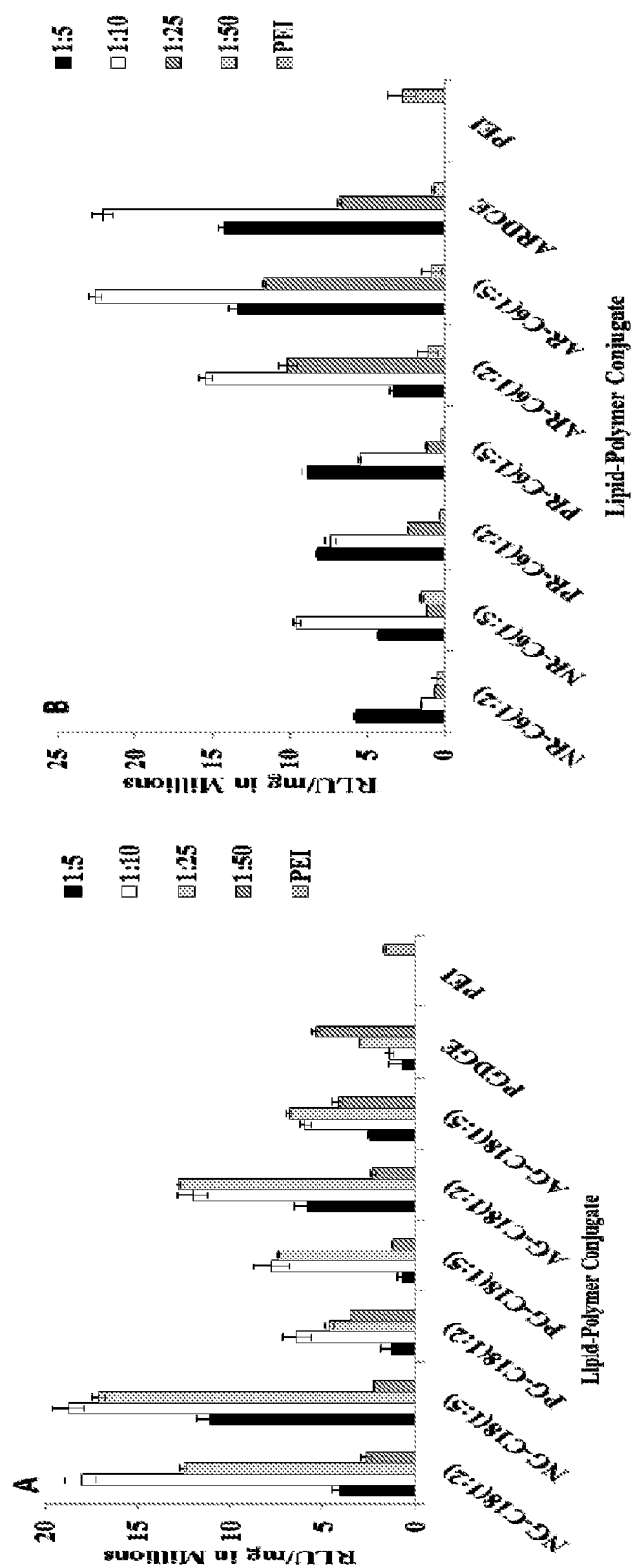
FIG. 14 graphically illustratrates in vitro transfection profiles of leads of lipid conjugated polymers, polymer lead and pEI at different weight ratios in PC3-PSMA cells.
Figure 15:
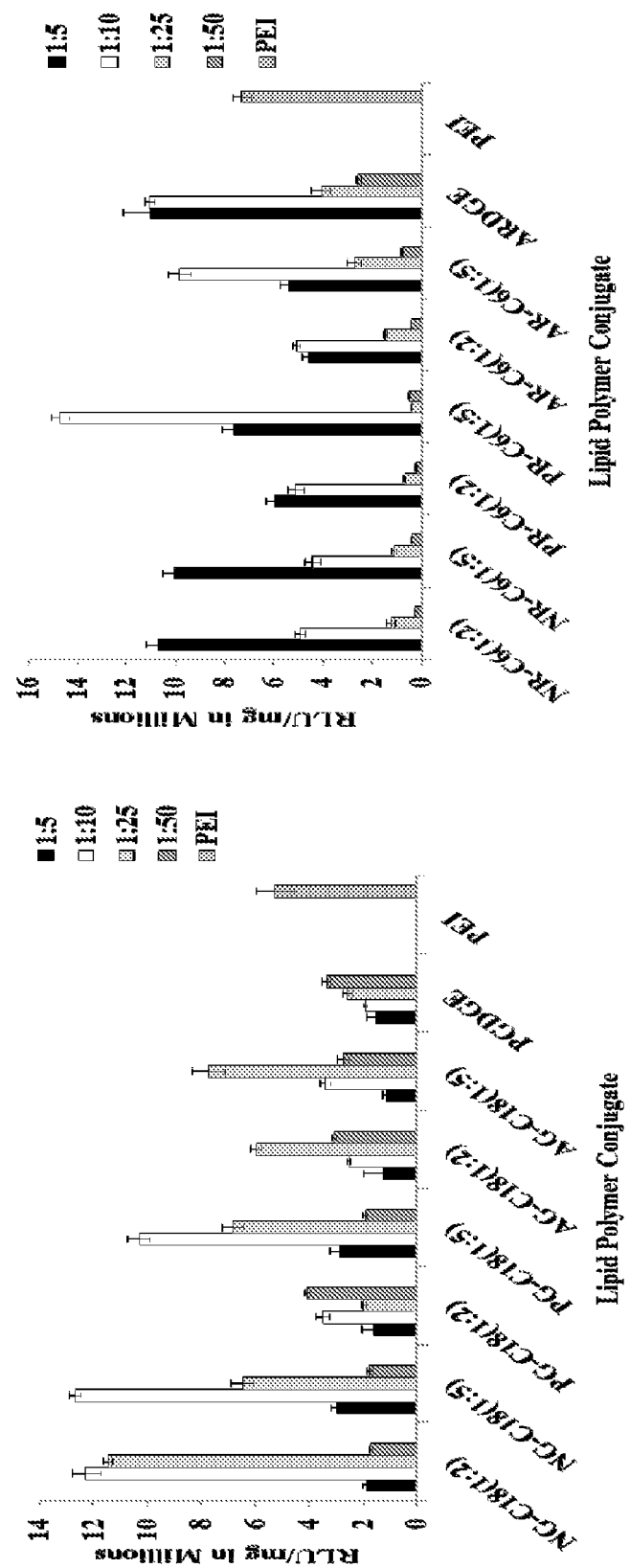
FIG. 15A graphically illustratrates in vitro transfection profiles of lipopolymers with Glycerol diglycidyl ether as linker group, conjugated polymers, polymer lead and pEI at different weight ratios in 22RV1 cells.
FIG. 15B graphically illustratrates in vitro transfection profiles of lipopolymers with Resorcinol diglycidyl ether as linker group, conjugated polymers, polymer lead and pEI at different weight ratios in 22RV1 cells.
Figure 22:
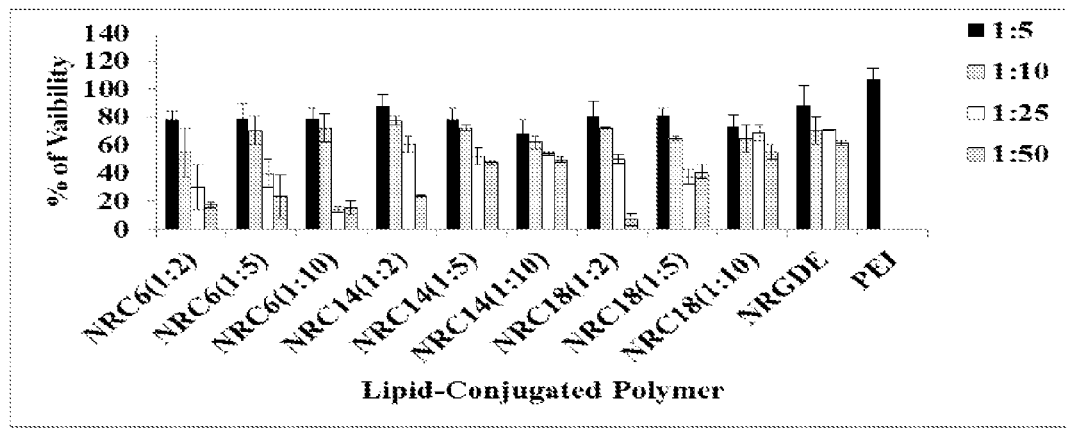
FIG. 22 graphically illustrates in vitro toxicity profiles of Neomycin-RDE polymer, Neomycin-RDE lipid polymer conjugates with varying lipids and varying molar ratios and pEI at different weight ratios in PC3 cells.
Figure 23:
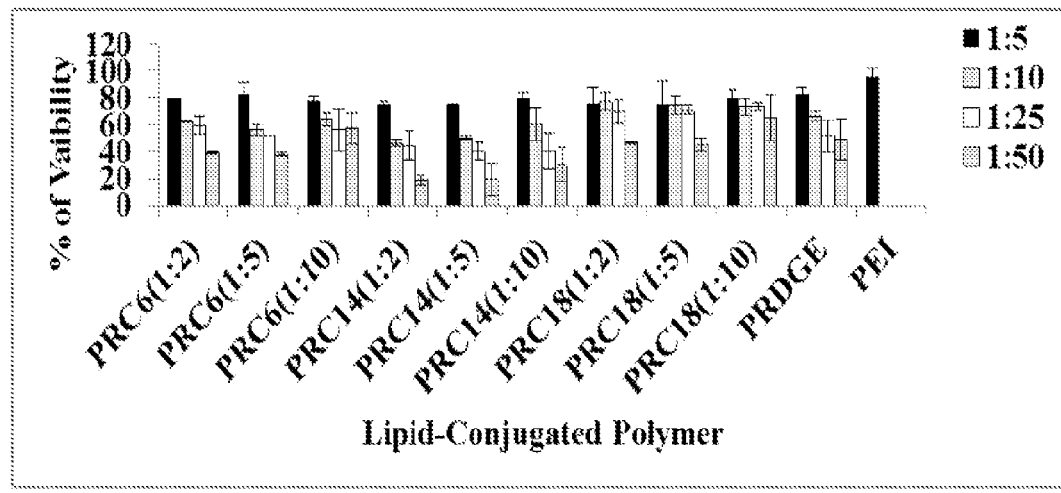
FIG. 23 graphically illustrates in vitro toxicity profiles of Paromomycin-RDE polymer, Paromomycin-RDE lipid polymer conjugates with varying lipids and varying molar ratios and pEI at different weight ratios in PC3 cells.
Figure 24:
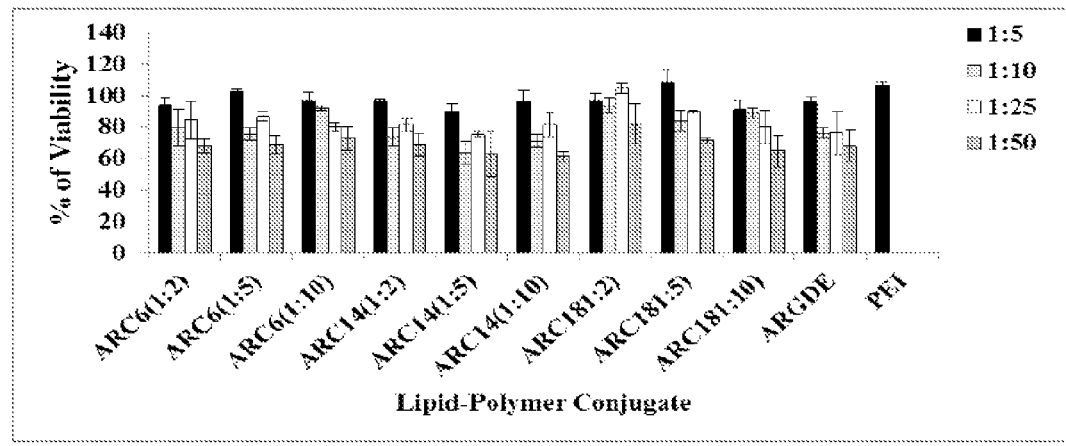
FIG. 24 graphically illustrates in vitro toxicity profiles of Apramycin-RDE polymer, Apramycin-RDE lipid polymer conjugates with varying lipids and varying molar ratios and pEI at different weight ratios in PC3 cells.

Applicants discovered that, in general, polymers based on glycerol diglycidyl ether as linker group showed better enhancement in transgene expression when conjugated with C18 lipid and polymers based on resorcinol diglycidyl ether showed better enhancement in transgene expression when conjugated with C6 lipids. We also found that the transgene expression also depends on the weight ratios of pDNA/lipopolymer used. We found that the transgene expression is also cell type dependent. The highest transgene expression were found in PC3 type of cells followed by PC3-PSMA FIGS. 14 and 22RV1 cells FIG. 15.

Cytotoxicities of the lipid conjugated polymers were assessed by the 3-(4,5-dimethylthiazol-2-yl)-2,5-diphenyltetrazolium bromide (MTT) reduction assay. In the present invention, the cytotoxicity assay was performed in 96-well plates by maintaining the same ratio of number of cells to amount of cationic DNA/lipopolymer complexes, as used in the transfection experiments. Briefly, the cells were incubated with lipopolyplexes for 6 h followed by the addition of 150 μL of serum containing media. After 48 hours of transfection,10 μL MTT (5 mg/mL in PBS) was added to each well and after 3-4 h of incubation at 37° C., 30 μL of the detergent was added to the cells and incubated for overnight. The absorbance was measured at 550 nm and results were expressed as percent viability=[A540 (treated cells)-background/A540 (untreated cells)-background]× 100.

The cytotoxicity studies of the entire 54 lipid conjugated polymers were evaluated in PC3 types of cells and the results were as shown in FIGS. 19-24. The toxicity profiles of all the lipid conjugated polymers were evaluated with respect to the parent polymer and the pEI-25 kDa. The toxicity profiles of the library of lipid conjugated polymers synthesized in general found to be increase on increasing the grafting ratios. The C18 lipid conjugated polymer is found to be slightly higher toxic to the smaller alkyl chain C6 conjugated polymers. The toxicity studies were conducted under the same conditions of the transfection studies with a DNA:lipopolymer weight ratios of 1:5 to 1:50. The PEI shown here is at a single weight ratio of 1:1 (the same ratio used for the transfection studies) and is found to be non-toxic. We found that the Apramycin based lipid conjugated polymers were the least toxic among all the lipid conjugated polymers.

Serum stability studies of the lead lipid conjugated polymers were carried out in PC3 types of cells with varying amounts of serum concentrations. The transfection experiments in presence of serum were carried out following the protocol used in in vitro transfection experiments. Only the difference is the cells are incubated with the lipopolyplexes for 6 hours at various concentrations of serum (varying from 0, 10, 30 and 50 percentage of serum). After 6 h of incubation the media is replaced with the 10% serum containing media and the remaining procedure is same as followed in in vitro transfection experiments.

Figure 17:
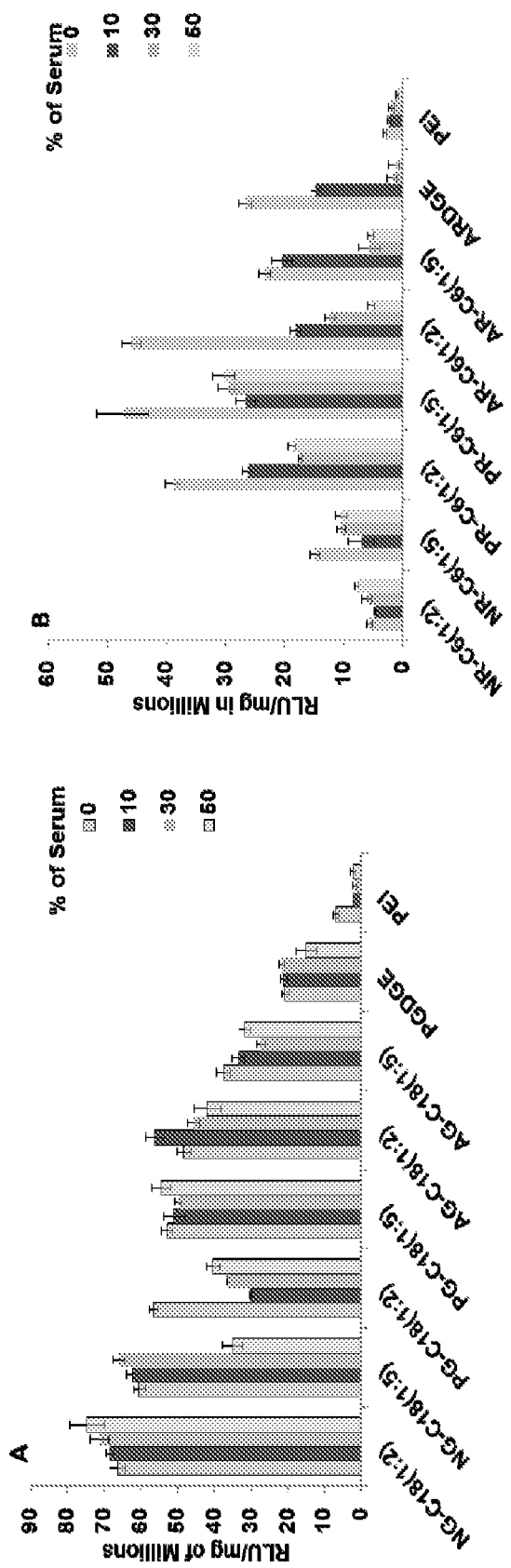
FIG. 17A graphically illustrates serum stability studies of leads of with lipopolymers with Glycerol diglycidyl ether as linker group and pEI at different concentrations of serum added in PC3 cells.
FIG. 17B graphically illustrates serum stability studies of leads of with lipopolymers with Resorcinol diglycidyl ether as linker group and pEI at different concentrations of serum added in PC3 cells.

Applicant found that the lipid conjugated polymers are serum stable. Among the different sets of conjugates the lipopolymers with glycerol diglycidyl ether linker are found to be more serum compatible even at higher concentrations of serum when compared to the lipopolymers with resorcinol diglycidyl ether as linker. We found that the Neomycin glycerol diglycidy ether based lipopolymers were found to be better serum compatible when compared to other leads. The serum stability of the leads from both the sets of lipopolymers is shown in FIG. 17.

Figure 16:
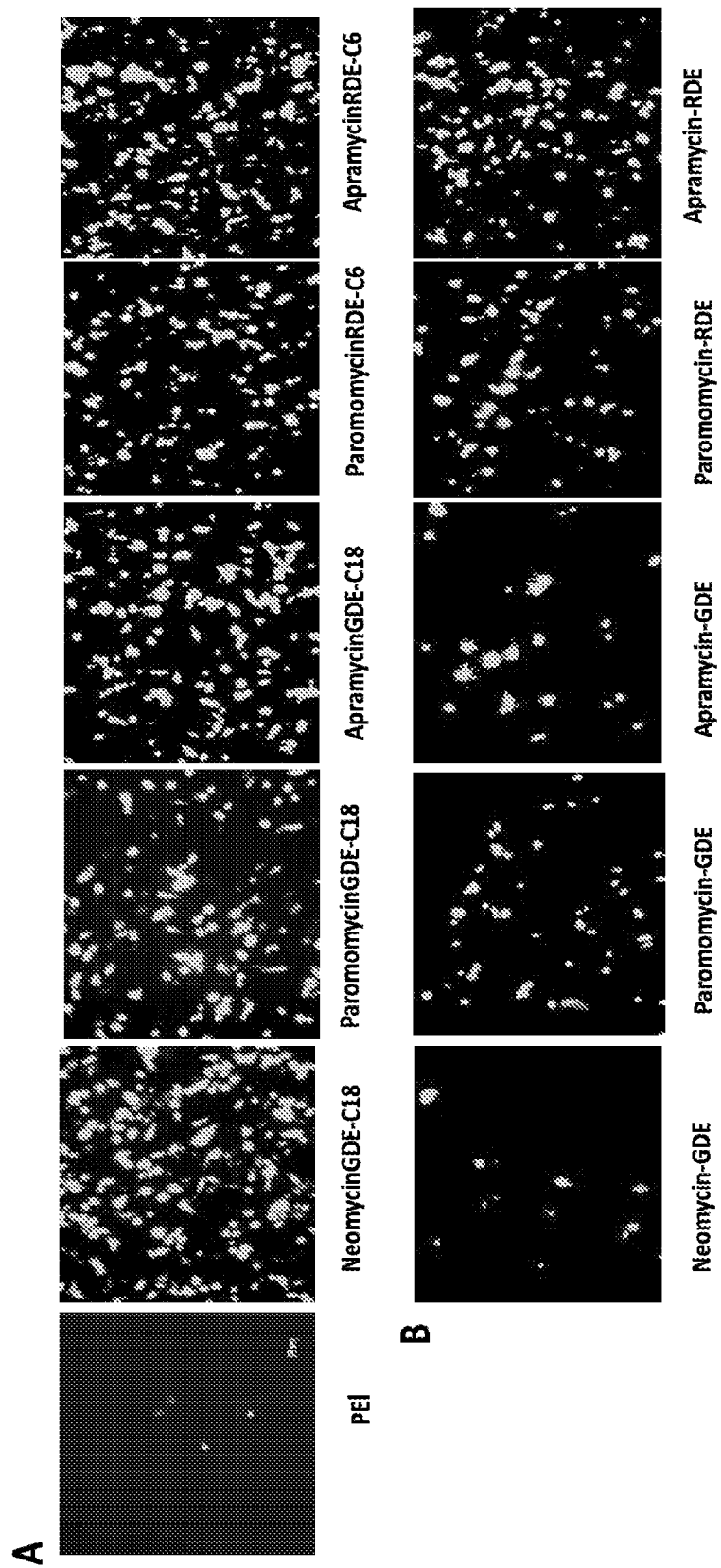
FIG. 16A illustrates green fluorescent image of leads of lipid conjugated polymers and PEI.
FIG. 16B illustrates green fluorescent image of polymer leads and pEI at higher transgene expression weight ratios in PC3 cells.

EF-GFP (enhanced green fluorescent protein)-encoding pDNA (pEFGFP) were delivered as described in in vitro transfection procedure. The transfection experiments were carried out and the green fluorescent protein expressed was observed using fluorescent microscope. FIG. 16 shows the GFP expression of the leads of lipid polymer conjugates, the respective parent polymers and pEI in PC3 types of cells.

Applicants found that in few conjugates there is a great enhancement in the GFP expression in the cells transfected with lipopolymers when compared to the cells transfected with only polymers. This is in accordance with the luciferase values observed form the in vitro transfection experiments.

DNA binding studies of the lipid conjugated polymers were studied using EtBr exclusion assay. Intercalation-induced fluorescence increase and competition with lipopolymers to bind to DNA has made EtBr an excellent tool to study lipopolymers-DNA interactions. To assess the representative lipopolymer-DNA interactions of the presently described leads of lipopolymer library, Applicants complexed EtBr:pGL4.5 complex with varying amounts of lipopolymers (using the indicated DNA/lipopolymer weight ratios of 1:5-1:50).

Figure 18:
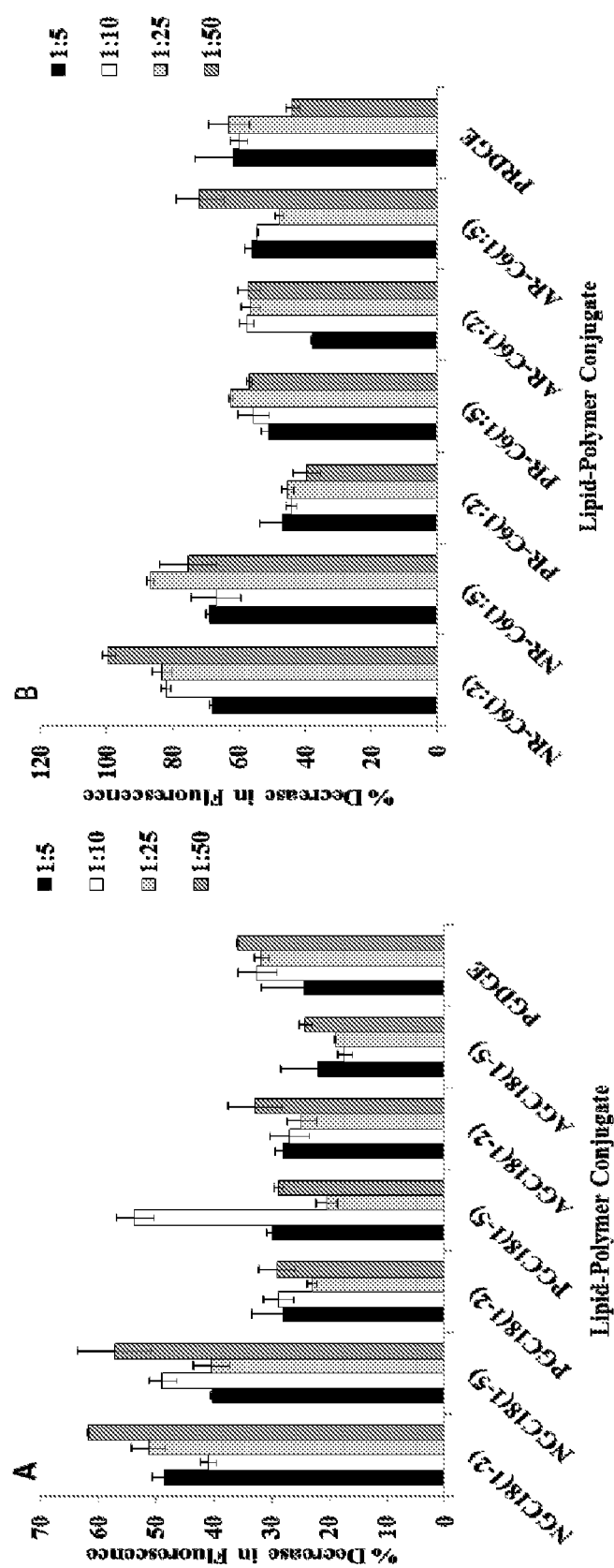
FIG. 18A graphically illustrates DNA binding profiles of leads of lipopolymers with Glycerol diglycidyl ether as linker group and pEI at different concentrations of serum added in PC3 cells; at different weight ratios used for in vitro transfection experiments.
FIG. 18B graphically illustrates DNA binding profiles of leads of lipopolymers with Resorcinol diglycidyl ether as linker group and pEI at different concentrations of serum added in PC3 cells; at different weight ratios used for in vitro transfection experiments.
Figure 19:
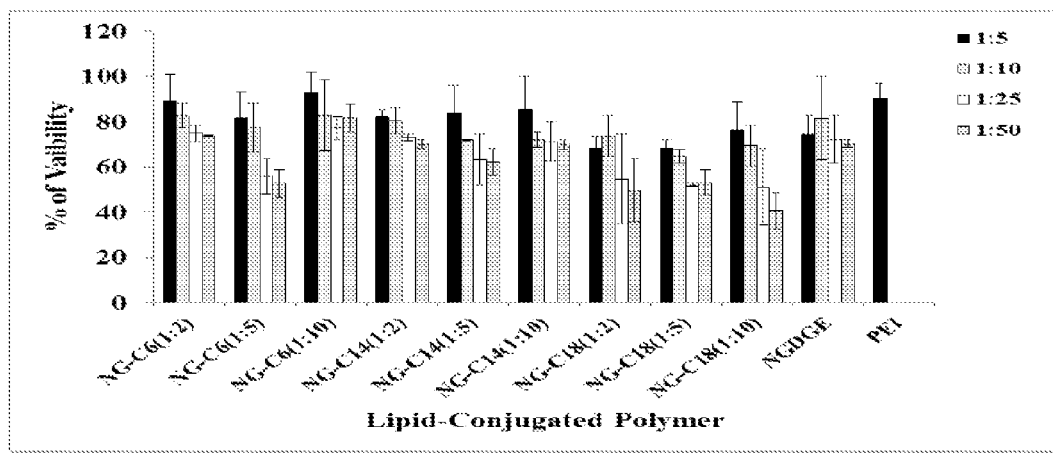
FIG. 19 graphically illustrates in vitro toxicity profiles of Neomycin-GDE polymer, Neomycin-GDE lipid polymer conjugates with varying lipids and varying molar ratios and pEI at different weight ratios in PC3 cells.
Figure 20:
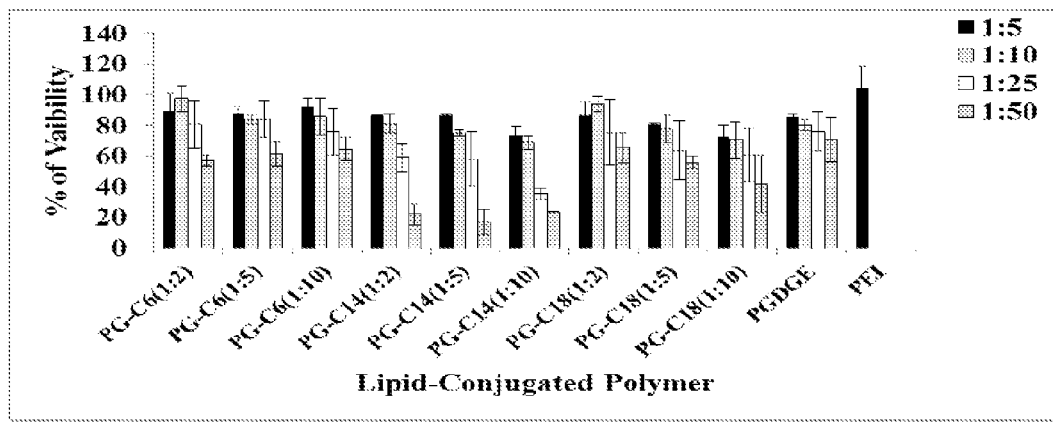
FIG. 20 graphically illustrates in vitro toxicity profiles of Paromomycin-GDE polymer, Paromomycin-GDE lipid polymer conjugates with varying lipids and varying molar ratios and pEI at different weight ratios in PC3 cells.
Figure 21:
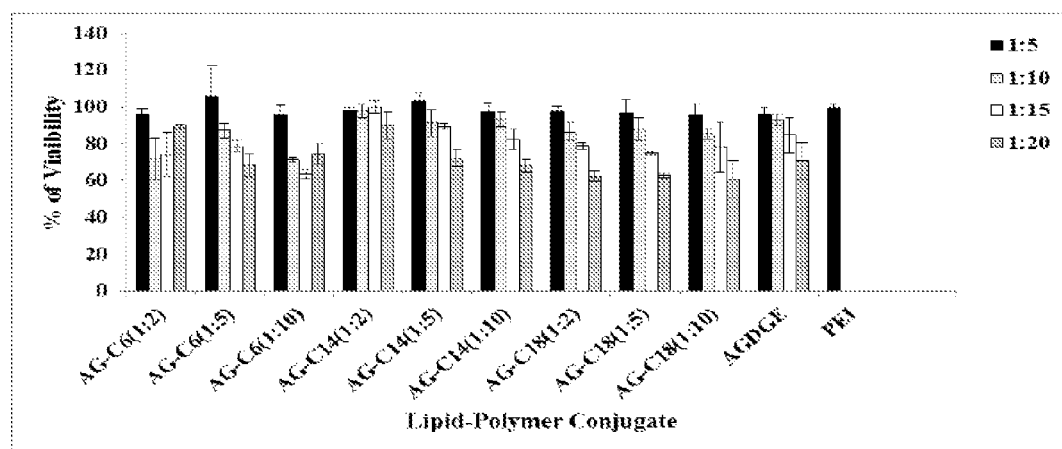
FIG. 21 graphically illustrates in vitro toxicity profiles of Apramycin-GDE polymer, Apramycin-GDE lipid polymer conjugates with varying lipids and varying molar ratios and pEI at different weight ratios in PC3 cells.

The data in FIG. 18 shows that all the leads of the lipopolymer library interact strongly with DNA at higher DNA/lipopolymer weight ratios i.e. at 1:25 and 1:50 as seen by their ability to exclude ethidium bromide form DNA. This further supports the results obtained in the invitro transfection experiments showing higher transfection values at the optimal DNA/polymer weight ratio is dependent on the DNA binding profiles of the lipopolymer.

Figure 25B:
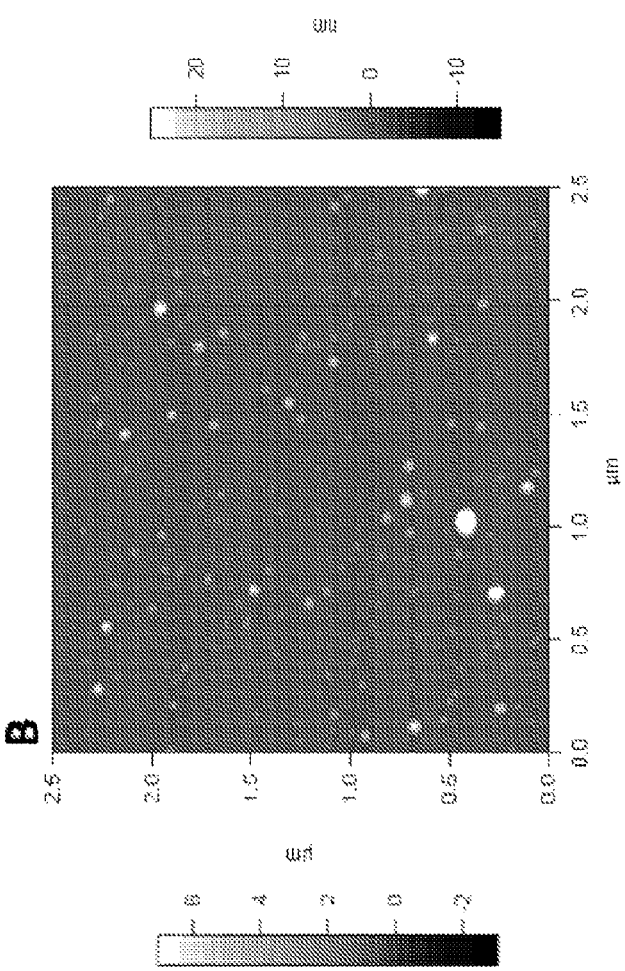
FIG. 25B recites an AFM image of Micelles of PRDGE Lipid Conjugated Polymer.
Figure 25A:
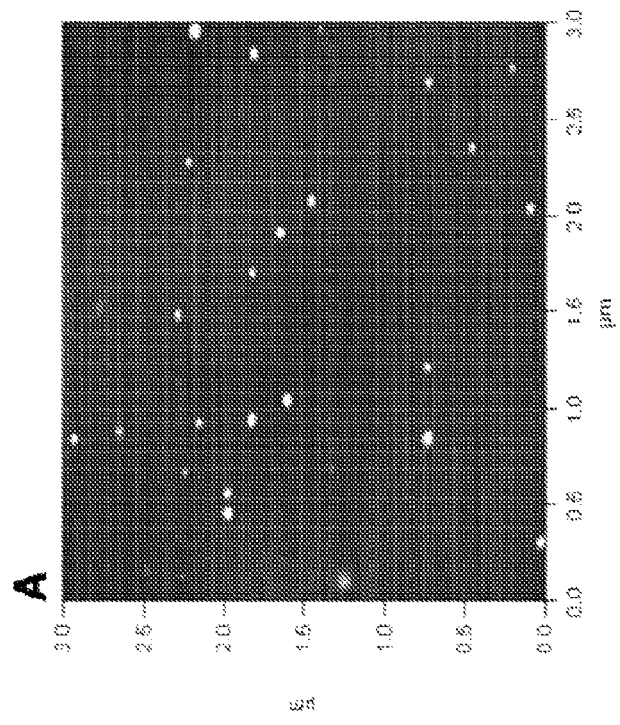
FIG. 25A recites an AFM image of Micelles of ARDGE Lipid Conjugated Polymer.

Applicants have carried out the AFM imaging studies of the lipid conjugated polymers that form the micelles. FIG. 25 shows the AFM images of two different samples of lipid conjugated Polymers that forms micelles. (ARDE polymer with C14 lipid conjugation and PRDE polymer with C14 lipid conjugation). These images are at different magnification. Atomic force microscopy (AFM, NanoScope III, Digital Instrument) equipped with an integrated silicon tip/cantilever with resonance frequency of ~240 kHz in height and phase image models were utilized for the observation of morphologies.

Polymer solutions (10 μL) were dropped on a mica sample stage and dried at room temperature for the morphological observation. The AFM images show that the particles are of various sizes. This may arise due to formation of aggregates or sometimes due to degradation during the process of drying.

In summary, Applicants designed and developed a library of lipid conjugated polymers by the reaction between lipid acid chlorides and the free amines on the lead polymers. A library of 54 lipopolymers were developed using six different polymers, three different acid chlorides and three different molar ratios. The degree of substitution was found to be dependent on the molar feed ratio of polymer to lipid. The screening of all the lipopolymer for luciferase transgene expression revealed that few lipopolymers are many times better in transgene expression when compared to their parent polymers.

One important observation is that few of the lead lipid conjugated polymers were found to be highly serum compatible even at higher concentrations of serum. This insinuates the possibility of using these leads further for in vivo studies.

Further the hydrophobic modification of the resorcinol diglycidyl ether based polymers developed supported the formation of micelles. These micelles will have greater applicability in the field of drug delivery, gene delivery and imaging studies. In this invention, we successfully developed various micelle of size ranging from 20-50 nm Taken together, lipid conjugated polymer library developed has potential to use as gene delivery vectors or as a material for drug delivery, imaging studies as well as combined drug and gene delivery.

Table 1 recites percentage degree of substitution of lead lipid conjugated polymers calculated based on the area under the NMR shifts.

TABLE 1

| Sample ID | Polymer (mmol) | Lipid (mmol) | Lipid/ Polymer (mol ratio)$^a$ | Lipid/ Polymer (mol ratio)$^b$ | (Degree of Subtn %)$^c$ |
| --- | --- | --- | --- | --- | --- |
| NGDGE-C18 | 0.01 | 0.02 | 2.0 | 0.65 | 9.33 |
| NGDGE-C18 | 0.01 | 0.05 | 5.0 | 0.98 | 14 |
| AGDGE-18 | 0.01 | 0.02 | 2.0 | 0.49 | 12.27 |
| AGDGE-C18 | 0.01 | 0.05 | 5.0 | 0.74 | 18.5 |
| PGDGE-C18 | 0.01 | 0.02 | 2.0 | 0.45 | 9 |
| PGDGE-C18 | 0.01 | 0.05 | 5.0 | 0.8 | 16 |
| PRGDE-C6 | 0.01 | 0.02 | 2.0 | 0.43 | 10.2 |
| PRGDE-C6 | 0.01 | 0.05 | 5.0 | 0.57 | 13 |
| PRGDE-C6 | 0.01 | 0.02 | 2.0 | 0.24 | 6.7 |
| PRGDE-C6 | 0.01 | 0.05 | 5.0 | 0.76 | 16.9 |
| PRGDE-C6 | 0.01 | 0.02 | 2.0 | 0.34 | 9.2 |
| PRGDE-C6 | 0.01 | 0.05 | 5.0 | 0.86 | 19.8 |

Table 2 recites molecular weights and polydispersity index of leads of lipid conjugated polymers.

TABLE 2

| S. No. | SAMPLE | Mn | Mw | PDI |
|---|---|---|---|---|
| 1 | NGDE-C18(1:2) | 3138 | 4088 | 1.3 |
| 2 | NGDE-C18(1:5) | 3241 | 4232 | 1.3 |
| 3 | PGDE-C18(1:2) | 3228 | 4345 | 1.34 |
| 4 | PGDE-C18(1:5) | 3485 | 4519 | 1.28 |
| 5 | AGDE-C18(1:2) | 2228 | 3551 | 1.59 |
| 6 | AGDE-C18(1:5) | 3118 | 3777 | 1.21 |
| 7 | ARDE-C6(l-2) | 2886 | 3570 | 1.23 |
| 8 | ARDE-C6(l-5) | 2827 | 3463 | 1.22 |
| 9 | PRDE-C6(l-2) | 3843 | 4962 | 1.18 |
| 10 | PRDE-C6(l-5) | 4057 | 5282 | 1.31 |
| 11 | NRDE-C6(l-2) | 3086 | 3814 | 1.16 |
| 12 | NRDE-C6(l-5) | 3489 | 4063 | 1.24 |

While the preferred embodiments of the present invention have been illustrated in detail, it should be apparent that modifications and adaptations to those embodiments may occur to one skilled in the art without departing from the scope of the present invention.

We claim:

1. A method to form an aminoglycoside based polymer, comprising:

reacting an aminoglycoside having a structure:

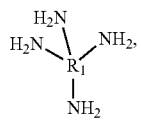

wherein $R_1$ is an aminoglycoside monomer, with a diepoxide having a structure:

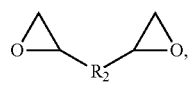

wherein $R_2$ is a backbone of said diepoxide, to form an aminoglycoside-based polymeric material having a structure:

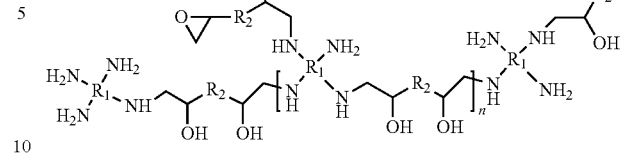

wherein n is between about 3 and about 10.

2. The method of claim 1, further comprising reacting said aminoglycoside-based polymeric material with an acyl chloride having a structure:

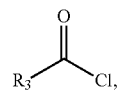

wherein $R_3$ is an alkyl group comprising $C_6$, $C_{14}$, or $C_{18}$, to form a lipid-containing aminoglycoside polymer having a structure:

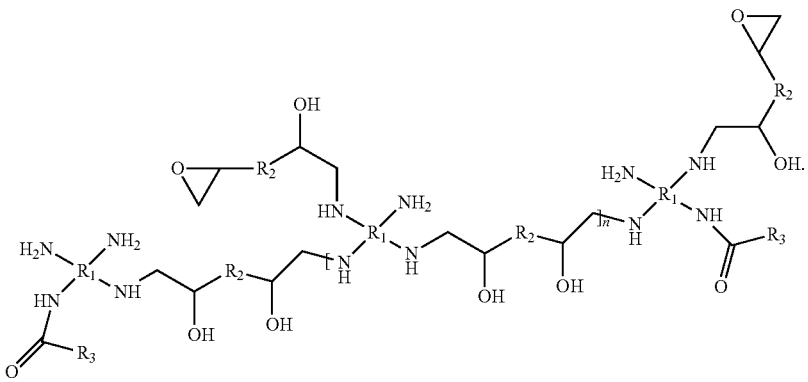

3. The method of claim 1, wherein said aminoglycoside comprises neomycin.

4. The method of claim 1, wherein said aminoglycoside comprises paromomycin.

5. The method of claim 1, wherein said aminoglycoside comprises apramycin.

6. The method of claim 1, wherein said diepoxide comprises glycerol diglycidyl ether.

7. The method of claim 1, wherein said diepoxide comprises resorcinol diglycidyl ether.

8. The method of claim 2, wherein the molar ratio of said acyl chloride to said aminoglycoside-based polymeric material is about 1:2.

9. The method of claim 2, wherein the molar ratio of said acyl chloride to said aminoglycoside-based polymeric material is about 1:5.

10. The method of claim 2, wherein the molar ratio of said acyl chloride to said aminoglycoside-based polymeric material is about 1:10.

11. The method of claim 2, wherein $R_3$ comprises a C6 hydrocarbon.

12. The method of claim 2, wherein $R_3$ comprises a C18 hydrocarbon.

13. A lipid-conjugated polymer, coprising:

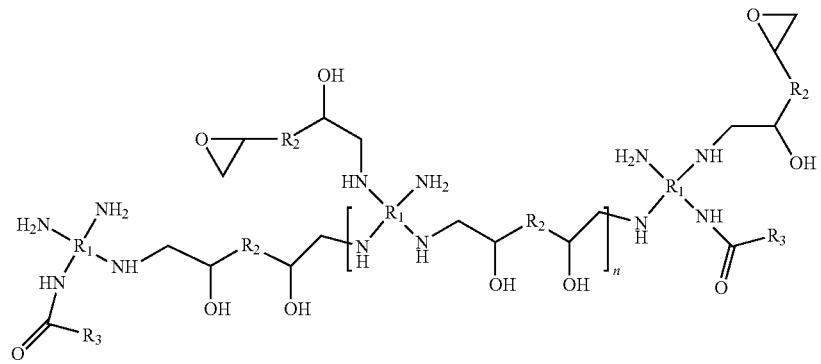

wherein $R_1$ is an aminoglycoside monomer, $R_2$ is a backbone of a diepoxide, and $R_3$ is an alkyl group comprising C6, C14, or C18.

14. A method to form an aminoglycoside based polymer, comprising:
reacting an aminoglycoside with a diepoxide in a solvent system of DMSO to form an aminoglycoside-based polymeric material.

15. The method of claim 14, further comprising reacting said aminoglycoside-based polymeric material with an acyl chloride to form a lipid-containing aminoglycoside polymer.

16. The method of claim 14, wherein the diepoxide comprises diglycidyl ether.

* * * * *